United States Patent
Fukaya et al.

(10) Patent No.: US 10,137,183 B2
(45) Date of Patent: Nov. 27, 2018

(54) PEPTIDE COMPOSITIONS HAVING 4 LINKED CTL EPITOPES AND USES THEREOF

(71) Applicant: TAIHO PHARMACEUTICAL CO., LTD., Tokyo (JP)

(72) Inventors: Satoshi Fukaya, Ibaraki (JP); Toshihiro Osada, Ibaraki (JP); Hiroshi Wada, Ibaraki (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 15/030,678

(22) PCT Filed: Oct. 20, 2014

(86) PCT No.: PCT/JP2014/077807
§ 371 (c)(1),
(2) Date: Apr. 20, 2016

(87) PCT Pub. No.: WO2015/060235
PCT Pub. Date: Apr. 30, 2015

(65) Prior Publication Data
US 2016/0235828 A1    Aug. 18, 2016

(30) Foreign Application Priority Data

Oct. 21, 2013 (JP) .................. 2013-218524
Jul. 30, 2014 (JP) .................. 2014-155132

(51) Int. Cl.
*A61K 39/00* (2006.01)
*C07K 14/00* (2006.01)
(Continued)

(52) U.S. Cl.
CPC ...... *A61K 39/0011* (2013.01); *C07K 14/4748* (2013.01); *C07K 14/70539* (2013.01);
(Continued)

(58) Field of Classification Search
CPC ............ A61K 39/0011; C07K 14/4748; C07K 14/70539; C07K 14/82
See application file for complete search history.

(56) References Cited

U.S. PATENT DOCUMENTS 6,719,976 B1    4/2004  Sone et al.
7,041,297 B1    5/2006  Itoh et al.
(Continued)

FOREIGN PATENT DOCUMENTS

CN    1218412 A     6/1999
CN    101854945 A   10/2010
(Continued)

OTHER PUBLICATIONS

International Search Report dated Jun. 17, 2014, in PCT/JP2014/055555.
(Continued)

*Primary Examiner* — Cherie Michelle Stanfield
(74) *Attorney, Agent, or Firm* — Foley & Lardner LLP

(57) ABSTRACT

This invention provides a cancer antigen peptide that can be administered to a wide range of cancer patients in the form of a peptide vaccine for cancer without the need for HLA typing and regardless of the HLA types of patients. Such peptide having 4 linked CTL epitopes is obtained by linking 4 CTL epitope peptides selected from among CTL epitope peptides derived from tumor antigen molecules that are reported to have the capacity for CTL induction via linkers.

13 Claims, 17 Drawing Sheets

Specification includes a Sequence Listing.

(51) Int. Cl.
　　　C07K 14/82　(2006.01)
　　　C07K 14/74　(2006.01)
　　　C07K 14/47　(2006.01)
(52) U.S. Cl.
　　　CPC ...... C07K 14/82 (2013.01); A61K 2039/5158
　　　　　(2013.01); A61K 2039/572 (2013.01); A61K
　　　　　2039/575 (2013.01); A61K 2039/70 (2013.01)

(56) References Cited

U.S. PATENT DOCUMENTS

| | | | | |
|---|---|---|---|---|
| 7,718,614 | B2* | 5/2010 | Itoh | A61K 31/565 |
| | | | | 424/185.1 |
| 9,102,715 | B2 | 8/2015 | Itoh | |
| 9,701,729 | B2* | 7/2017 | Fukaya | A61K 39/0011 |
| 2002/0128201 | A1* | 9/2002 | Itoh | C12N 9/1205 |
| | | | | 424/185.1 |
| 2003/0175288 | A1 | 9/2003 | Itoh | |
| 2004/0044188 | A1 | 3/2004 | Feige et al. | |
| 2006/0008463 | A1 | 1/2006 | Itoh et al. | |
| 2006/0140968 | A1 | 6/2006 | Itoh et al. | |
| 2007/0055049 | A1 | 3/2007 | Grey et al. | |
| 2008/0014186 | A1 | 1/2008 | Itoh et al. | |
| 2008/0014636 | A1 | 1/2008 | Sato et al. | |
| 2008/0119399 | A1 | 5/2008 | Itoh et al. | |
| 2008/0286228 | A1 | 11/2008 | Tarantolo et al. | |
| 2010/0062010 | A1 | 3/2010 | Nishihara et al. | |
| 2010/0278851 | A1 | 11/2010 | Itoh et al. | |
| 2010/0297187 | A1 | 11/2010 | Stoloff et al. | |
| 2013/0164314 | A1 | 6/2013 | Itoh et al. | |

FOREIGN PATENT DOCUMENTS

| | | | | |
|---|---|---|---|---|
| EA | 005404 | B1 | 2/2005 | |
| EP | 0923940 | B1 | 6/1999 | |
| EP | 2192407 | A2 | 6/2010 | |
| EP | 2196209 | A1 | 6/2010 | |
| EP | 2966092 | A1 | 1/2016 | |
| JP | 11-318455 | A | 11/1999 | |
| JP | WO 0111044 | A1 * | 2/2001 | C12N 9/1205 |
| JP | 2002-527050 | A | 8/2002 | |
| JP | 2003-000270 | A | 1/2003 | |
| JP | 2003-512057 | A | 4/2003 | |
| JP | 2007-145715 | A | 6/2007 | |
| JP | 2010-000083 | A | 1/2010 | |
| JP | 2012-158597 | A | 8/2012 | |
| RU | 2466737 | C2 | 10/2011 | |
| WO | WO 97/32600 | A1 | 9/1997 | |
| WO | WO 99/67288 | A1 | 12/1999 | |
| WO | WO 00/12701 | A1 | 3/2000 | |
| WO | WO 00/21551 | A1 | 4/2000 | |
| WO | WO 01/11044 | A1 | 2/2001 | |
| WO | WO 01/29220 | A2 | 4/2001 | |
| WO | WO 01/41741 | A1 | 6/2001 | |
| WO | WO 02/10369 | A1 | 2/2002 | |
| WO | WO 2004/029248 | A1 | 4/2004 | |
| WO | WO 2005/071075 | A1 | 8/2005 | |
| WO | WO 2005/116056 | A1 | 12/2005 | |
| WO | WO 2008/007711 | A1 | 1/2008 | |
| WO | WO 2009/022652 | A1 | 2/2009 | |
| WO | WO 2009/038026 | A1 | 3/2009 | |
| WO | WO 2012/005161 | A1 | 1/2012 | |

OTHER PUBLICATIONS

Ishioka et al., "Utilization of MHC Class I Transgenic Mice for Development of Minigene DNA Vaccines Encoding Multiple HLA-Restricted CTL Epitopes," The Journal of Immunology, 1999, 162:3915-3925.

Lee et al., "Increased Vaccine-Specific T Cell Frequency After Peptide-Based Vaccination Correlates with Increased Susceptibility to In Vitro Stimulation But Does Not Lead to Tumor Regression," The Journal of Immunology, 1999, 163:6292-6300.
Office Action and Search Report dated Aug. 29, 2016, in RU 2015142659, with English translation.
Office Action dated Mar. 8, 2016, in JP 2015-504352.
Search Report dated Oct. 19, 2016 in EP 14761112.3.
Skosyrev et al., "The dependence of stability of the green fluorescent protein-obelin hybrids on the nature of their constituent modules and the structure of the amino acid linker," Bioorg. Khim., Sep.-Oct. 2001, 27(5):364-371, with English translation.
Taiwanese Office Action dated Jan. 21, 2015 in TW 103108019.
Zhao et al., "Balancing the Pharmacokinetics and Pharmacodynamics of Interferon-α2b and Human Serum Albumin Fusion Protein by Proteolytic or Reductive Cleavage Increases In Vivo Therapeutics Efficacy," Mol. Pharm., 2012, 9(3):664-670.
Freshney, Culture of Animal Cells, A Manual of Basic Technique, Alan R. Liss, Inc., 1983, New York, p. 4.
Dermer, Bio/Technology, 1994, 12:320.
Gura, Science, 1997, 278:1041-1042.
Jain, Sci. Am., 1994, 271:58-65.
Ezzell, J. NIH Res., 1995, 7:46.
Spitler, Cancer Biotherapy, 1995, 10:1-3.
Boon, Adv. Can. Res., 1992, 58:177-210.
Nelson et al., Ann. Intern. Med., 2009, 151:727-737.
Kataja et al., Ann. Oncol., 2009, 20(Supp. 4):iv10-14.
Haigh et al., Oncology, 1999, 13:1561.
Balmana et al., Ann. Oncol., 2009, 20(Supp. 4):iv19-20.
International Search Report dated Jan. 20, 2015, in PCT/JP2014/077807.
Noguchi et al., "Assessment of immunological biomarkers in patients with advanced cancer treated by personalized peptide vaccination," Cancer Biology & Therapy, Dec. 15, 2010, 10(12):1266-1279.
Noguchi et al., "A randomized phase II trial of personalized peptide vaccine plus low dose estramustine phosphate (EMP) versus standard dose EMP in patients with castration resistant prostate cancer," Cancer Immunol. Immunother., 2010, 59(7):1001-1009.
Rosenberg et al., "Cancer immunotherapy: moving beyond current vaccines," Nature Medicine, Sep. 2004, 10(9):909-915.
Sette et al., "Nine major HLA class I supertypes account for the vast preponderance of HLA-A and -B polymorphism," Immunogenetics, 1999, 50(3-4):201-212.
Terasaki et al., "Phase I Trial of a Personalized Peptide Vaccine for Patients Positive for Human Leukocyte Antigen-A24 With Recurrent or Progressive Glioblastoma Multiforme," Journal of Clinical Oncology, Jan. 20, 2011, 29(3):337-344.
Yanagimoto et al., "Immunological evaluation of personalized peptide vaccination with gemcitabine for pancreatic cancer," Cancer Sci., Apr. 2007, 98(4):605-611.
Supplementary European Search Report dated Jul. 18, 2017, in EP 14856540.1.
Liao et al., "Diepitope multiple antigen peptide of hTERT trigger stronger anti-tumor immune responses in vitro," International Immunopharmacology, May 25, 2013, 16(4):444-450.
Van der Burg et al., "Improved peptide vaccine strategies, creating synthetic artificial infections to maximize immune efficacy," Advanced Drug Delivery Reviews, Aug. 12, 2006, 58(8):916-930.
Office Action dated Aug. 2, 2018, in CN 201480057880.4.
Chen et al., "Advances in anti-tumor research of CTL epitope polypeptide vaccine," Journal of Clinical Medicine in Practice, 2008, 12(1):38-46, with partial English translation.
Qing-Feng et al., "In Vitro Specific anti-Chronic Myeloid Leukemia Cell Effect of CTL by a Multiple Epitope BCR-ABL Fusion Protein," Letters in Biotechnology, Jul. 2009, 20(4):517-519, English abstract on p. 517.

* cited by examiner

Fig. 1-3
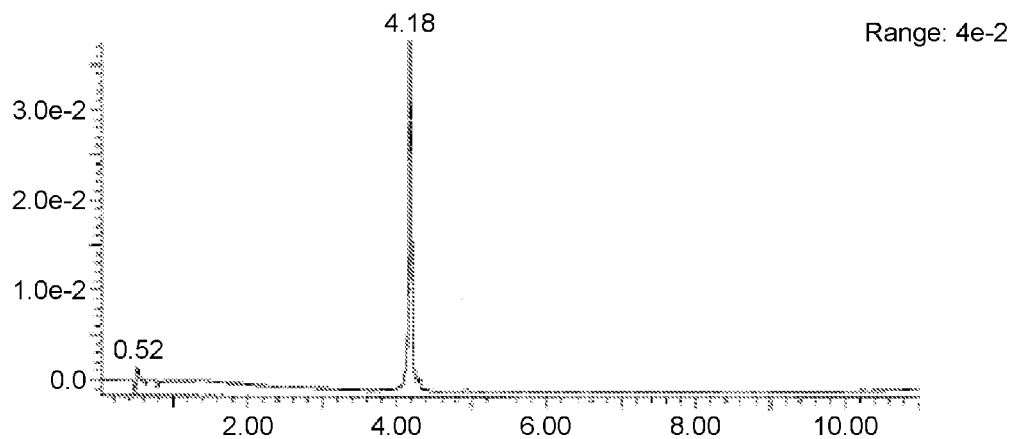
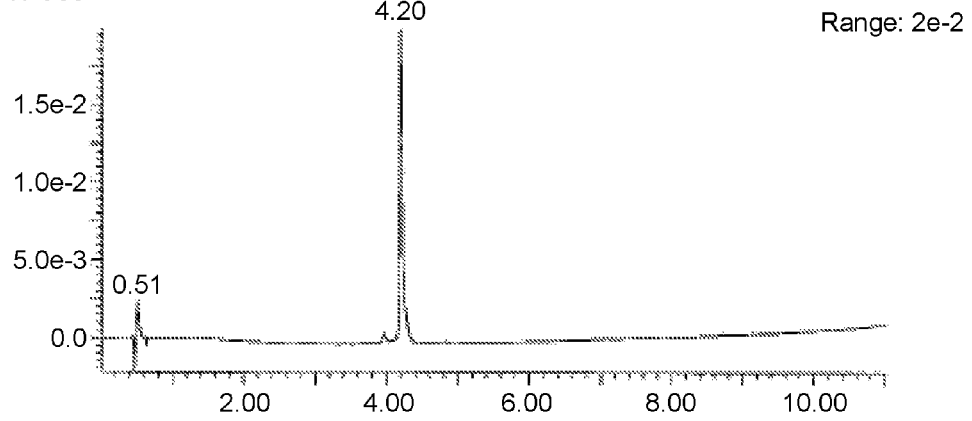

Fig. 1-4
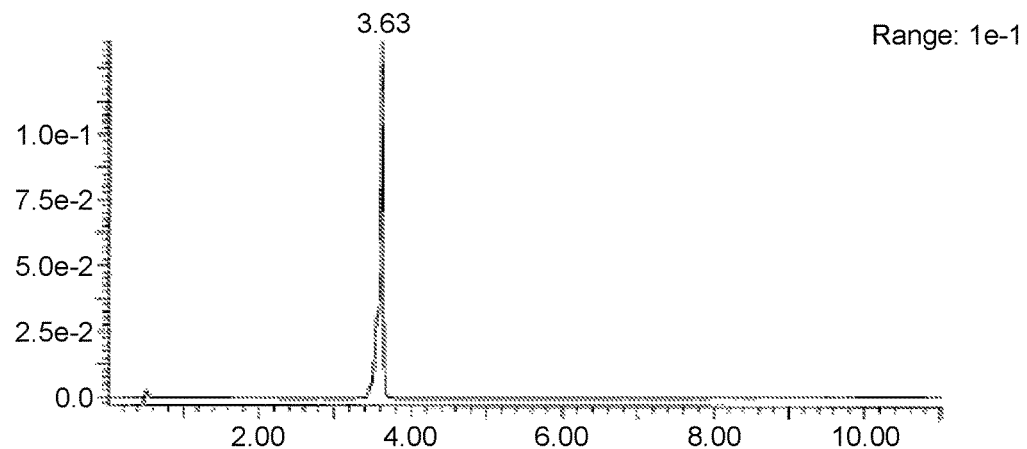
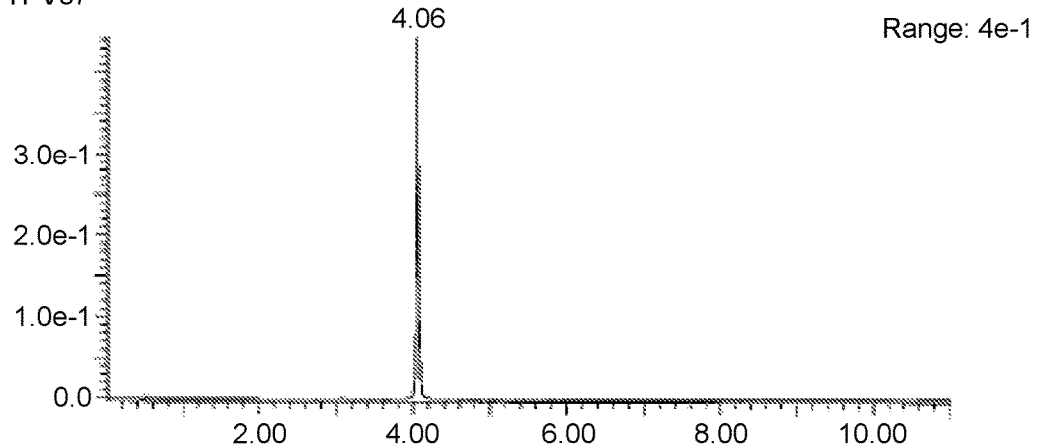

Fig. 1-5
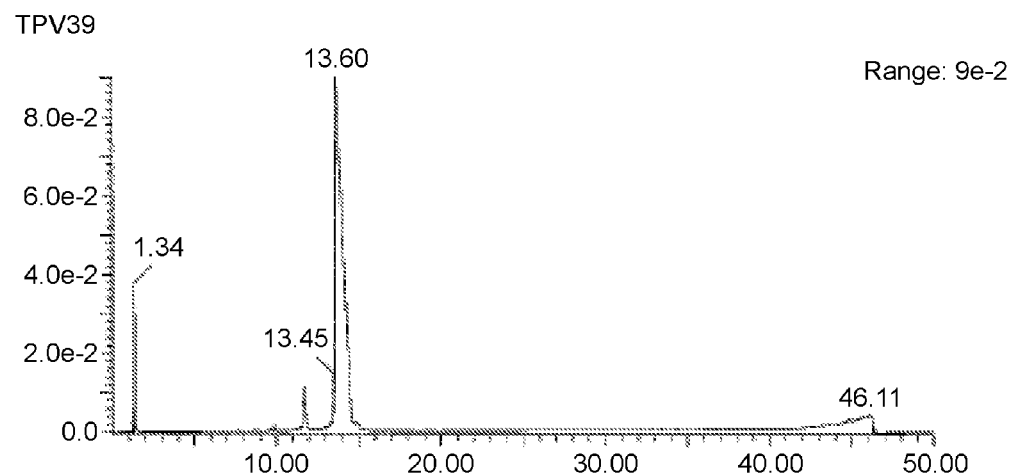
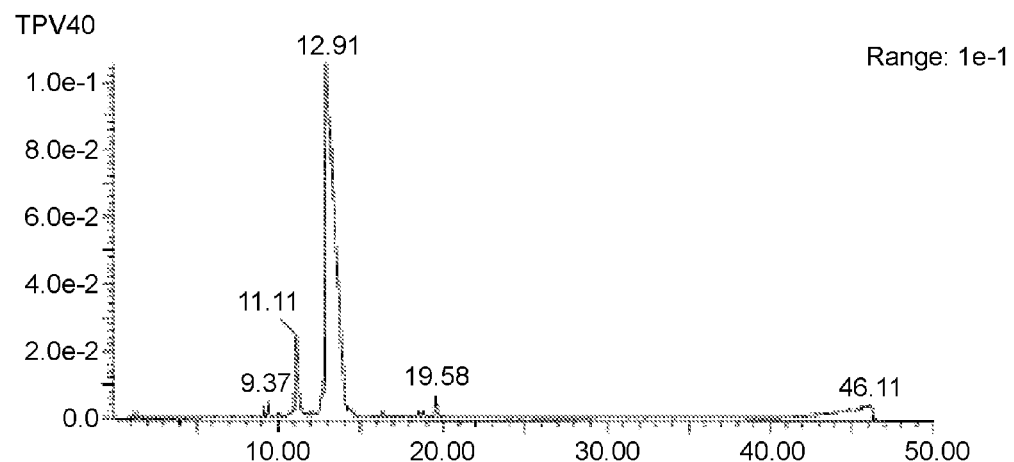

Fig. 1-6
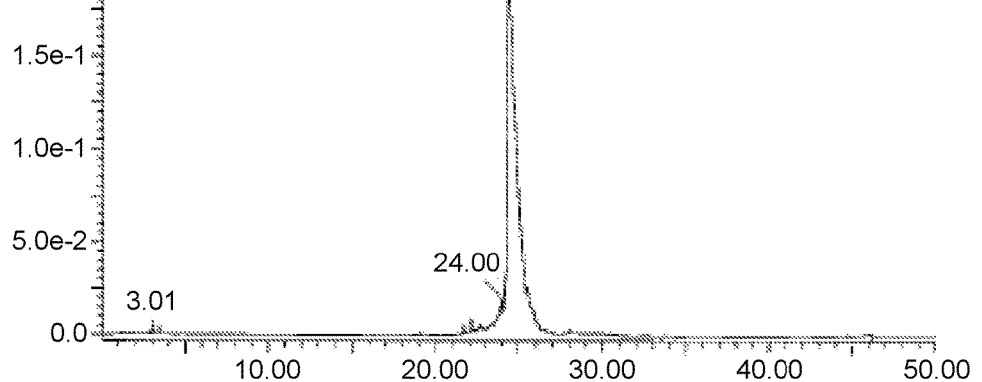
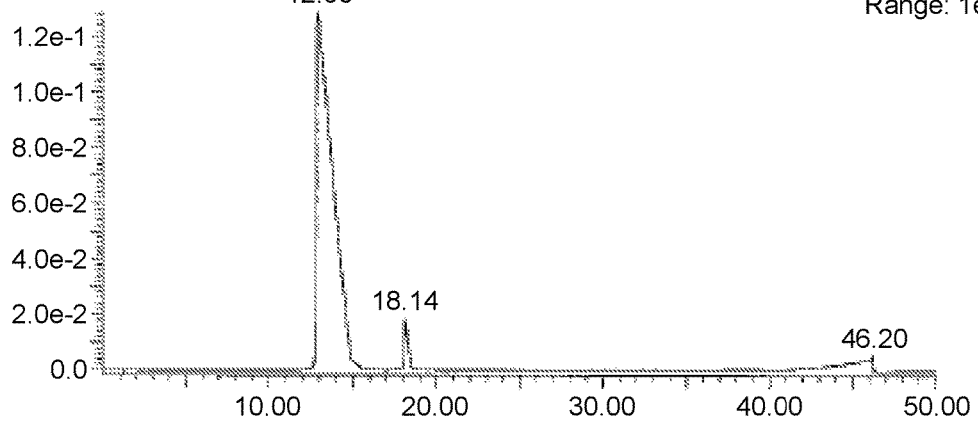

Fig. 3-1

| Conjugate administered | Epitope specific CTL induction | | | | PEP2 cleaved with i20S | PEP10 cleaved with i20S |
|---|---|---|---|---|---|---|
| | N terminus | | | C terminus | | |
| TPV01 | PEP5 | PEP6 | PEP9* | PEP4 | / | / |
| TPV02 | PEP9* | PEP5 | PEP6 | PEP4 | / | / |
| TPV03 | PEP6 | PEP5 | PEP9* | PEP4 | / | / |
| TPV04 | PEP6 | PEP9* | PEP5 | PEP4 | / | / |
| TPV05 | PEP9* | PEP6 | PEP5 | PEP4 | / | / |
| TPV06 | PEP5 | PEP9* | PEP6 | PEP4 | / | / |
| TPV07 | PEP1 | PEP7 | PEP8* | PEP2* | O | / |
| TPV08 | PEP1 | PEP8* | PEP7 | PEP2* | O | / |
| TPV09 | PEP7 | PEP1 | PEP8* | PEP2* | O | / |
| TPV10 | PEP8* | PEP7 | PEP1 | PEP2* | O | / |
| TPV11 | PEP8* | PEP1 | PEP7 | PEP2* | O | / |
| TPV12 | PEP7 | PEP13 | PEP8* | PEP2* | O | / |
| TPV13 | PEP8* | PEP13 | PEP7 | PEP2* | O | / |
| TPV14 | PEP13 | PEP7 | PEP8* | PEP2* | O | / |
| TPV15 | PEP8* | PEP7 | PEP13 | PEP2* | O | / |
| TPV16 | PEP13 | PEP8* | PEP7 | PEP2* | O | / |
| TPV17 | PEP13 | PEP15 | PEP18 | PEP10* | / | O |
| TPV18 | PEP13 | PEP18 | PEP15 | PEP10* | / | O |
| TPV19 | PEP15 | PEP13 | PEP18 | PEP10* | / | O |

Fig. 3-2

| Conjugate administered | Epitope specific CTL induction | | | | PEP2 cleaved with i20S | PEP10 cleaved with i20S |
|---|---|---|---|---|---|---|
| | N terminus | | | C terminus | | |
| TPV20 | PEP15 | PEP18 | PEP13 | PEP10* | | O |
| TPV21 | PEP18 | PEP13 | PEP15 | PEP10* | | O |
| TPV22 | PEP18 | PEP15 | PEP13 | PEP10* | | O |
| TPV23 | PEP1 | PEP15 | PEP18 | PEP10* | | O |
| TPV24 | PEP1 | PEP18 | PEP15 | PEP10* | | O |
| TPV25 | PEP15 | PEP1 | PEP18 | PEP10* | | O |
| TPV26 | PEP15 | PEP18 | PEP1 | PEP10* | | O |
| TPV27 | PEP18 | PEP1 | PEP15 | PEP10* | | O |
| TPV28 | PEP18 | PEP15 | PEP1 | PEP10* | | O |
| TPV29 | PEP15 | PEP17 | PEP13 | PEP10* | | * |
| TPV30 | PEP15 | PEP13 | PEP17 | PEP10* | | * |
| TPV31 | PEP17 | PEP15 | PEP13 | PEP10* | | * |
| TPV32 | PEP17 | PEP13 | PEP15 | PEP10* | | * |
| TPV33 | PEP13 | PEP17 | PEP15 | PEP10* | | * |
| TPV34 | PEP13 | PEP15 | PEP17 | PEP10* | | * |
| TPV37 | PEP1 | PEP7 | PEP6 | PEP5 | | |
| TPV38 | PEP7 | PEP1 | PEP6 | PEP5 | | |
| TPV35 | PEP6 | PEP18 | PEP5 | PEP9* | | |
| TPV36 | PEP6 | PEP5 | PEP18 | PEP9* | | |

Fig. 3-3

| Conjugate administered | Epitope specific CTL induction | | | | PEP2 cleaved with i20S | PEP10 cleaved with i20S |
|---|---|---|---|---|---|---|
| | N terminus | | | C terminus | | |
| CPV01 | PEP18 | PEP17 | PEP14 | PEP12* | / | / |
| CPV02 | PEP11* | PEP15 | PEP19 | PEP16 | / | / |
| CPV03 | PEP11* | PEP16 | PEP15 | PEP19 | / | / |
| CPV04 | PEP11* | PEP19 | PEP15 | PEP16 | / | / |
| CPV05 | PEP15 | PEP11* | PEP16 | PEP19 | / | / |
| CPV06 | PEP14 | PEP12* | PEP13 | PEP17 | / | / |
| CPV07 | PEP17 | PEP14 | PEP13 | PEP12* | / | / |
| CPV08 | PEP17 | PEP13 | PEP18 | PEP14 | / | / |
| CPV09 | PEP13 | PEP12* | PEP14 | PEP18 | / | / |
| CPV10 | PEP17 | PEP12* | PEP14 | PEP18 | / | / |
| CPV11 | PEP17 | PEP13 | PEP12* | PEP14 | / | / |
| CPV12 | PEP17 | PEP18 | PEP14 | PEP12* | / | / |
| CPV13 | PEP17 | PEP18 | PEP14 | PEP13 | / | / |
| CPV14 | PEP7 | PEP8* | PEP1 | PEP2* | O | / |
| CPV15 | PEP7 | PEP8* | PEP13 | PEP2* | * | / |
| CPV16 | PEP2* | PEP9* | PEP4 | PEP5 | * | / |

| | |
|---|---|
| p>0.05 | |
| p<0.05, 10≦Δ<100 | ▨ |
| p<0.05, 100≦Δ<200 | ▰ |
| p<0.05, 200≦Δ | ■ |

| | |
|---|---|
| Uncleavable | / |
| Cleavable | O |
| Unexamined | * |

Fig. 3-4

| Conjugate administered | Epitope specific CTL induction | | | | PEP2 cleaved with i20S | PEP10 cleaved with i20S |
|---|---|---|---|---|---|---|
| | N terminus | | | C terminus | | |
| TPV39 | PEP7 | PEP13 | PEP8* | PEP2* | O | / |
| TPV40 | PEP7 | PEP13 | PEP8* | PEP2* | O | / |
| TPV41 | PEP7 | PEP13 | PEP8* | PEP2* | / | / |
| TPV42 | PEP5 | PEP9* | PEP6 | PEP4 | / | / |
| TPV43 | PEP5 | PEP9* | PEP6 | PEP4 | / | / |
| TPV44 | PEP15 | PEP18 | PEP1 | PEP10* | / | / |
| TPV45 | PEP15 | PEP18 | PEP1 | PEP10* | / | / |

| | |
|---|---|
| $p > 0.05$ | |
| $p < 0.05, 10 \leq \Delta < 100$ | ▨ |
| $p < 0.05, 100 \leq \Delta < 200$ | ▨ |
| $p < 0.05, 200 \leq \Delta$ | ■ |

| | |
|---|---|
| Uncleavable | / |
| Cleavable | O |
| Unexamined | * |

Fig. 4-1

|  | Epitope specific IgG (fold induction vs. IFA) | | | |
|---|---|---|---|---|
| mixture1 | PEP10 | PEP13 | PEP15 | PEP18 |
| mixture2 | PEP4 | PEP5 | PEP6 | PEP9 |
| mixture3 | PEP1 | PEP2 | PEP7 | PEP8 |
| mixture4 | PEP1 | PEP10 | PEP15 | PEP18 |

| Conjugate administered | N terminus | | | C terminus |
|---|---|---|---|---|
| TPV01 | PEP5 | PEP6 | PEP9 | PEP4 |
| TPV02 | PEP9 | PEP5 | PEP6 | PEP4 |
| TPV03 | PEP6 | PEP5 | PEP9 | PEP4 |
| TPV04 | PEP6 | PEP9 | PEP5 | PEP4 |
| TPV05 | PEP9 | PEP6 | PEP5 | PEP4 |
| TPV06 | PEP5 | PEP9 | PEP6 | PEP4 |
| TPV07 | PEP1 | PEP7 | PEP8 | PEP2 |
| TPV08 | PEP1 | PEP8 | PEP7 | PEP2 |
| TPV09 | PEP7 | PEP1 | PEP8 | PEP2 |
| TPV10 | PEP8 | PEP7 | PEP1 | PEP2 |
| TPV11 | PEP8 | PEP1 | PEP7 | PEP2 |
| TPV12 | PEP7 | PEP13 | PEP8 | PEP2 |
| TPV13 | PEP8 | PEP13 | PEP7 | PEP2 |
| TPV14 | PEP13 | PEP7 | PEP8 | PEP2 |
| TPV15 | PEP8 | PEP7 | PEP13 | PEP2 |
| TPV16 | PEP13 | PEP8 | PEP7 | PEP2 |
| TPV17 | PEP13 | PEP15 | PEP18 | PEP10 |
| TPV18 | PEP13 | PEP18 | PEP15 | PEP10 |
| TPV19 | PEP15 | PEP13 | PEP18 | PEP10 |

Fig. 4-2

| Conjugate administered | N terminus | | | C terminus |
|---|---|---|---|---|
| TPV20 | PEP15 | PEP18 | PEP13 | PEP10 |
| TPV21 | PEP18 | PEP13 | PEP15 | PEP10 |
| TPV22 | PEP18 | PEP15 | PEP13 | PEP10 |
| TPV23 | PEP1 | PEP15 | PEP18 | PEP10 |
| TPV24 | PEP1 | PEP18 | PEP15 | PEP10 |
| TPV25 | PEP15 | PEP1 | PEP18 | PEP10 |
| TPV26 | PEP15 | PEP18 | PEP1 | PEP10 |
| TPV27 | PEP18 | PEP1 | PEP15 | PEP10 |
| TPV28 | PEP18 | PEP15 | PEP1 | PEP10 |
| TPV29 | PEP15 | PEP17 | PEP13 | PEP10 |
| TPV30 | PEP15 | PEP13 | PEP17 | PEP10 |
| TPV31 | PEP17 | PEP15 | PEP13 | PEP10 |
| TPV32 | PEP17 | PEP13 | PEP15 | PEP10 |
| TPV33 | PEP13 | PEP17 | PEP15 | PEP10 |
| TPV34 | PEP13 | PEP15 | PEP17 | PEP10 |
| TPV37 | PEP1 | PEP7 | PEP6 | PEP5 |
| TPV38 | PEP7 | PEP1 | PEP6 | PEP5 |

| | |
|---|---|
| fold<2 | |
| 2<fold<10 | |
| 10<fold<100 | |
| 100<fold | |

Fig. 4-3

| Conjugate administered | Epitope specific IgG (fold induction vs. IFA) | | | |
|---|---|---|---|---|
| | N terminus | | | C terminus |
| TPV39 | PEP7 | PEP13 | PEP8 | PEP2 |
| TPV40 | PEP7 | PEP13 | PEP8 | PEP2 |
| TPV41 | PEP7 | PEP13 | PEP8 | PEP2 |

| | |
|---|---|
| fold<2 | |
| 2<fold<10 | (diagonal hatching) |
| 10<fold<100 | (reverse diagonal hatching) |
| 100<fold | (black) |

PEPTIDE COMPOSITIONS HAVING 4 LINKED CTL EPITOPES AND USES THEREOF

TECHNICAL FIELD

The present invention relates to a novel peptide that is useful as a cancer antigen peptide. More particularly, the present invention relates to a novel cancer antigen peptide having 4 linked peptides capable of induction of HLA-A-restricted CTL responses and a pharmaceutical composition utilizing the same.

BACKGROUND ART

Cancer is the top cause of death in Japan. Approximately 350,000 patients die of cancer every year, and cancer is still a serious disease nowadays. The treatment approaches for cancer that have been established are surgical resection, anti-cancer drug treatment, and radiation treatment. However, such treatment strategies are problematic in terms of, for example, recurrence, decline in quality of life (QOL), and lack of treatment options in the case of advanced-stage cancers that cannot be treated with the strategies described above.

Cancer immunotherapy (cancer vaccines) has been expected as a novel therapeutic technique for a long period of time, and clinical studies on peptide vaccines for cancer were initiated throughout the world in 1990 when epitope peptides in human tumor antigens became identifiable. According to the results of analysis of clinical studies conducted via administration of a peptide alone or in combination with other agents, however, the response rate is as low as 2.7% among 1,000 or more cases (Rosenberg S A et al., Nature Med., 2004, 10 (9): 909-15). Thus, difficulty in practical application has been pointed out.

Meanwhile, clinical studies involving the use of particular peptide vaccines for cancer have been underway for a long period of time in Japan, and the achievements of such studies have gradually been articulated. In recent years, a strategy of administration of a multiple cancer peptides instead of a single type of cancer peptide has been attempted, with the aim of improving the outcome for treatment. For example, the HLA type and specific immune responses of a patient are examined in advance, so as to implement a tailor-made cancer treatment using peptide vaccines comprising selecting multiple adequate peptides to be administered, and safety and anti-tumor effects thereof have been verified. Through administration of tailor-made peptide vaccines alone or in combination with anti-cancer drugs, more specifically, excellent clinical effects and safety have been achieved in cases of brain tumor, uterine cervix cancer, prostate cancer, and pancreatic cancer (Terasaki, M. et al., J. Clin. Oncol., 2011, 29 (3): 337-44; Noguchi, M. et al., Cancer Immunol. Immunother., 2010, 59 (7): 1001-9; Yanagimoto, H. et al., Cancer Sci., 2007, 98 (4): 605-11).

The cell-mediated immunity consisting of epitope specific cytotoxic T lymphocytes (hereafter, abbreviated as "CTL"), which are considered to be major effector cells in cancer treatment using peptide vaccines, is HLA-restrictive. Accordingly, development of peptide vaccines for cancer exclusively targeting patients with a particular HLA type, specifically HLA-A2 or HLA-A24 type, has been attempted because of the large number of patients therewith.

However, Japanese people with such two HLA types account for approximately 40% and 60%, respectively (Sette, A. et al., Immunogenetics, 1999, 50 (3-4): 201-12). Disadvantageously, patients with other HLA types cannot gain benefits from peptide vaccines for cancer. In addition, the time of initiation of treatment would be postponed because of HLA typing performed prior to the initiation of treatment, and it would increase the burden on patients. Accordingly, research and development of peptide vaccines for cancer that are applicable to all cancer patients without HLA typing are desired.

Regarding cancer treatment using peptide vaccines, in addition to activations of CTLs as one of the cell-mediated immunity, inductions of production of immunoglobulins known as the humoral immunity is known to be attributable to survival benefit (Noguchi, M. et al., Cancer Biol. Ther., 2011, 10 (12):1266-79).

SUMMARY OF THE INVENTION

Objects to be Attained by the Invention

An object of the present invention is to provide a cancer antigen peptide that can be administered as a peptide vaccine for cancer to a wide range of cancer patients and that can strongly induce immunoglobulins, regardless of the HLA types of patients.

Means for Attaining the Objects

The present inventors obtained a peptide having 4 linked CTL epitopes by linking, via linkers, 4 peptides selected from among CTL epitope peptides reported to be capable of induction of HLA-A2, HLA-A24, HLA-A26, or HLA-A3 supertype-restricted CTL response or a plurality of HLA-A-restricted CTL responses. The present inventors have conducted concentrated studies on such peptide having 4 linked CTL epitopes in order to attain the above objects. As a result, they discovered that a peptide having 4 linked CTL epitopes composed of particular 13 types of peptides selected from among known tumor antigen molecule-derived CTL epitope peptides could be administered to a wide range of cancer patients without the need for HLA typing and regardless of the HLA types of patients. They also discovered that administration of such peptide having 4 linked CTL epitopes could strongly induce immunoglobulins, in addition to CTLs specific for CTL epitope peptides composing such peptide. This has led to the completion of the present invention.

Specifically, the present invention has the following features.

[1] A peptide having 4 linked epitopes, wherein the 4 epitope peptides are selected, optionally redundantly, from the group consisting of CTL epitope peptides: the peptide as shown in SEQ ID NO: 1 (PEP1); the peptide as shown in SEQ ID NO: 2 (PEP2); the peptide as shown in SEQ ID NO: 4 (PEP4); the peptide as shown in SEQ ID NO: 5 (PEP5); the peptide as shown in SEQ ID NO: 6 (PEP6); the peptide as shown in SEQ ID NO: 7 (PEP7); the peptide as shown in SEQ ID NO: 8 (PEP8); the peptide as shown in SEQ ID NO: 9 (PEP5); the peptide as shown in SEQ ID NO: 10 (PEP10); the peptide as shown in SEQ ID NO: 13 (PEP13); the peptide as shown in SEQ ID NO: 15 (PEP15); the peptide as shown in SEQ ID NO: 17 (PEP17); and the peptide as shown in SEQ ID NO: 18 (PEP18), linked via linkers, the peptide having 4 linked epitopes optionally comprise other peptide sequences consisting of hydrophilic amino acids, and the peptide having 4 linked epitopes has one or more features selected from the features (1) to (5) below:

(1) the peptide comprises PEP2 at the C terminus (except for the peptide comprising PEP7 and PEP8 at the N terminus successively disposed in such order from the N terminus via a linker);

(2) the peptide comprises PEP4 at the C terminus;

(3) the peptide comprises PEP10 at the C terminus;

(4) the peptide comprises PEP6 and PEP5 at the C terminus successively disposed in such order from the N terminus via a linker; and (5) the peptide comprises PEP5, PEP6, PEP9, and PEP18.

[2] The peptide having 4 linked epitopes according to [1], which comprises 4 non-redundant peptides selected from among PEP1, PEP2, PEP4, PEP5, PEP6, PEP7, PEP8, PEP9, PEP10, PEP13, PEP15, PEP17, and PEP18.

[3] The peptide having 4 linked epitopes according to [1] or [2] having any one of features selected from the features (1) to (5) below:

(1) the peptide comprises 3 CTL epitope peptides selected from among PEP1, PEP7, PEP8, and PEP13, and PEP2 is disposed at the C terminus of the peptide (except for the peptide comprising PEP7 and PEP8 at the N terminus successively disposed in such order from the N terminus via a linker);

(2) the peptide comprises 3 CTL epitope peptides, PEP5, PEP6, and PEP9, and PEP4 is disposed at the C terminus of the peptide;

(3) the peptide comprises 3 CTL epitope peptides selected from among PEP1, PEP13, PEP15, PEP17, and PEP18, and PEP10 is disposed at the C terminus of the peptide;

(4) the peptide comprises 2 CTL epitope peptides, PEP1 and PEP7, and PEP6 and PEP5 are successively disposed at the C terminus in such order from the N terminus via a linker; and (5) the peptide comprises 3 CTL epitope peptides, PEP5, PEP6, and PEP18, and PEP9 is disposed at the C terminus of the peptide.

[4] The peptide having 4 linked epitopes according to any of [1] to [3], which comprises a sequence selected from the following sequences, wherein "-(L)-" represents a linker:

PEP5-(L)-PEP6-(L)-PEP9-(L)-PEP4;
PEP9-(L)-PEP5-(L)-PEP6-(L)-PEP4;
PEP6-(L)-PEP5-(L)-PEP9-(L)-PEP4;
PEP6-(L)-PEP9-(L)-PEP5-(L)-PEP4;
PEP9-(L)-PEP6-(L)-PEP5-(L)-PEP4;
PEP5-(L)-PEP9-(L)-PEP6-(L)-PEP4;
PEP1-(L)-PEP7-(L)-PEP8-(L)-PEP2;
PEP1-(L)-PEP8-(L)-PEP7-(L)-PEP2;
PEP7-(L)-PEP1-(L)-PEP8-(L)-PEP2;
PEP8-(L)-PEP7-(L)-PEP1-(L)-PEP2;
PEP8-(L)-PEP1-(L)-PEP7-(L)-PEP2;
PEP7-(L)-PEP13-(L)-PEP8-(L)-PEP2;
PEP8-(L)-PEP13-(L)-PEP7-(L)-PEP2;
PEP13-(L)-PEP7-(L)-PEP8-(L)-PEP2;
PEP8-(L)-PEP7-(L)-PEP13-(L)-PEP2;
PEP13-(L)-PEP8-(L)-PEP7-(L)-PEP2;
PEP13-(L)-PEP15-(L)-PEP18-(L)-PEP10;
PEP13-(L)-PEP18-(L)-PEP15-(L)-PEP10;
PEP15-(L)-PEP13-(L)-PEP18-(L)-PEP10;
PEP15-(L)-PEP18-(L)-PEP13-(L)-PEP10;
PEP18-(L)-PEP13-(L)-PEP15-(L)-PEP10;
PEP18-(L)-PEP15-(L)-PEP13-(L)-PEP10;
PEP1-(L)-PEP15-(L)-PEP18-(L)-PEP10;
PEP1-(L)-PEP18-(L)-PEP15-(L)-PEP10;
PEP15-(L)-PEP1-(L)-PEP18-(L)-PEP10;
PEP15-(L)-PEP18-(L)-PEP1-(L)-PEP10;
PEP18-(L)-PEP1-(L)-PEP15-(L)-PEP10;
PEP18-(L)-PEP15-(L)-PEP1-(L)-PEP10;
PEP15-(L)-PEP17-(L)-PEP13-(L)-PEP10;
PEP15-(L)-PEP13-(L)-PEP17-(L)-PEP10;
PEP17-(L)-PEP15-(L)-PEP13-(L)-PEP10;
PEP17-(L)-PEP13-(L)-PEP15-(L)-PEP10;
PEP13-(L)-PEP17-(L)-PEP15-(L)-PEP10;
PEP13-(L)-PEP15-(L)-PEP17-(L)-PEP10;
PEP6-(L)-PEP18-(L)-PEP5-(L)-PEP9;
PEP6-(L)-PEP5-(L)-PEP18-(L)-PEP9;
PEP1-(L)-PEP7-(L)-PEP6-(L)-PEP5; and
PEP7-(L)-PEP1-(L)-PEP6-(L)-PEP5.

[5] The peptide having 4 linked epitopes according to any of [1] to [4], wherein the linker is an amino acid linker.

[6] The peptide having 4 linked epitopes according to any of [1] to [5], wherein the amino acid linker is an arginine dimer or arginine trimer composed of two or three arginine residues linked to each other.

[7] The peptide having 4 linked epitopes according to any of [1] to [6], wherein the other peptide sequence consisting of hydrophilic amino acids is linked to the N terminus.

[8] The peptide having 4 linked epitopes according to any of [1] to [7], wherein the other peptide sequence consisting of hydrophilic amino acids is composed of an arginine trimer or arginine tetramer composed of three or four arginine residues linked to each other.

[9] The peptide having 4 linked epitopes according to any of [1] to [8], which consists of the amino acid sequence as shown in SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, or SEQ ID NO: 66.

[10] A CTL obtained by stimulating peripheral blood lymphocytes using the peptide having 4 linked epitopes according to any of [1] to [9].

[11] A pharmaceutical composition comprising, as an active ingredient, the peptide having 4 linked epitopes according to any of [1] to [9] or the CTL according to [10].

[12] A pharmaceutical composition comprising two or more peptides selected from among the peptides having 4 linked epitopes according to any of [1] to [9].

[13] The pharmaceutical composition according to [11] or [12], which is an immunotherapeutic agent.

[14] A method for treatment of cancer comprising administering the peptide having 4 linked epitopes according to any of [1] to [9], the CTL according to [10], or the pharmaceutical composition according to any of [11] to [13] to a cancer patient.

This description includes part or all of the content as disclosed in the descriptions and/or drawings of Japanese Patent Application Nos. 2013-218524 and 2014-155132, which are priority documents of the present application.

Effects of the Invention

The present invention can provide a cancer antigen peptide that can be administered to a wide range of cancer patients as a peptide vaccine for cancer and that can strongly induce immunoglobulins, regardless of the HLA types of patients.

The peptide having 4 linked CTL epitopes according to the present invention can be administered to a wide range of cancer patients without the need for HLA typing. Examples of such patients include those who are HLA-A2 positive patients, HLA-A24 positive patients, HLA-A26 positive patients, and HLA-A3 supertype positive patients. The peptide as described above can be used for treatment and/or prevention of cancer or diseases caused thereby of such patients. In addition, expression of the tumor antigens constituting the peptide having 4 linked CTL epitopes according to the present invention is observed in a plurality of types of cancers. Accordingly, the peptide having 4 linked CTL epitopes according to the present invention can be used as a pharmaceutical composition (and more specifically, as an immunotherapeutic agent) for treatment and/or prevention of a variety of cancers. Through administration of the peptide having 4 linked epitopes according to the present invention, further, CTL epitope peptide specific CTLs and immunoglobulins can be induced more strongly, in comparison with administration of a mixture of an equivalent amount of CTL epitope peptides, and antitumor immunity can be more efficiently activated.

BRIEF DESCRIPTION OF THE DRAWINGS

FIG. 1-2 is a continuation from FIG. 1-1.
FIG. 1-3 is a continuation from FIG. 1-2.
FIG. 1-4 is a continuation from FIG. 1-3.
FIG. 1-5 is a continuation from FIG. 1-4.
FIG. 1-6 is a continuation from FIG. 1-5.
FIG. 1-7 is a continuation from FIG. 1-6.
FIG. 2-1 shows the results of mass spectrometry (MS) for the peptides having 4 linked epitopes obtained in Example 1 (TPV39, TPV40, TPV41, TPV43, and TPV45).
FIG. 2-2 is a continuation from FIG. 2-1.
FIG. 2-3 is a continuation from FIG. 2-2.

FIG. 3-1 shows the results of epitope specific CTL induction in mouse models to which the peptide having 4 linked epitopes has been administered (*: unexamined). FIG. 3-1 further shows the results of evaluation attained by cleaving the peptide having 4 linked epitopes with human immunoproteasomes and inspecting the cleavage of the C terminus of the identified PEP2 or PEP10 epitope peptide.

FIG. 3-2 is a continuation from FIG. 3-1.
FIG. 3-3 is a continuation from FIG. 3-2.
FIG. 3-4 shows the results of epitope specific CTL induction in mouse models to which the peptide having 4 linked epitopes comprising a peptide sequence of arginine residues at the N terminus or peptide having 4 linked epitopes comprising an arginine trimer as a peptide-peptide linker has been administered (*: unexamined). FIG. 3-4 further shows the results of evaluation attained by cleaving the peptide having 4 linked epitopes with human immunoproteasomes and inspecting the cleavage of the C terminus of the identified PEP2 or PEP10 epitope peptide.

FIG. 4-1 shows the results of assay of the epitope specific IgG antibody titer in sera of mouse models to which the peptide having 4 linked epitopes has been administered.

FIG. 4-2 is a continuation from FIG. 4-1.

FIG. 4-3 shows the results of assay of the epitope specific IgG antibody titer in sera of mouse models to which the peptide having 4 linked epitopes comprising a peptide sequence of arginine residues at the N terminus or peptide having 4 linked epitopes comprising an arginine trimer as a peptide-peptide linker has been administered.

EMBODIMENTS FOR CARRYING OUT THE INVENTION

Figure 1:
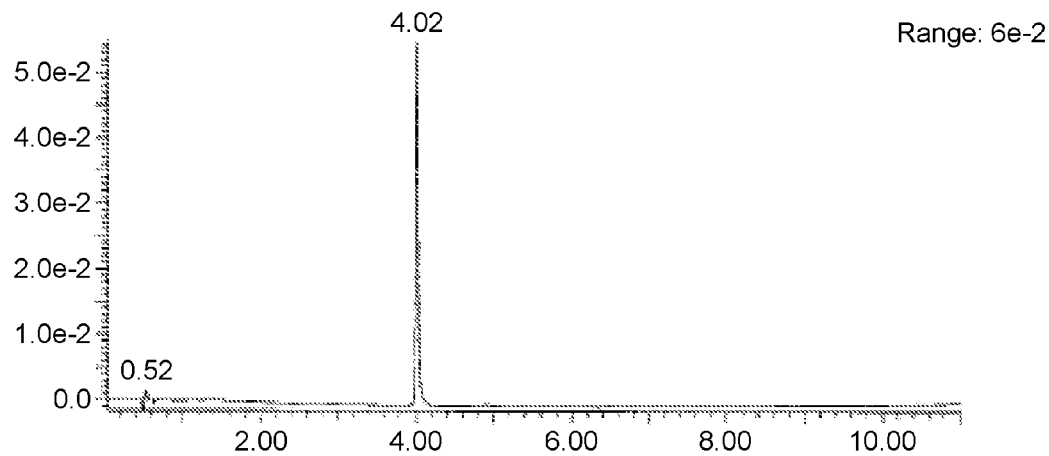
FIG. 1-1 shows the results of HPLC for the peptides having 4 linked epitopes obtained in Example 1 (TPV06, TPV10, TPV12, TPV21, TPV26, TPV30, TPV35, TPV37, TPV39, TPV40, TPV41, TPV43, and TPV45).
Figure 1:
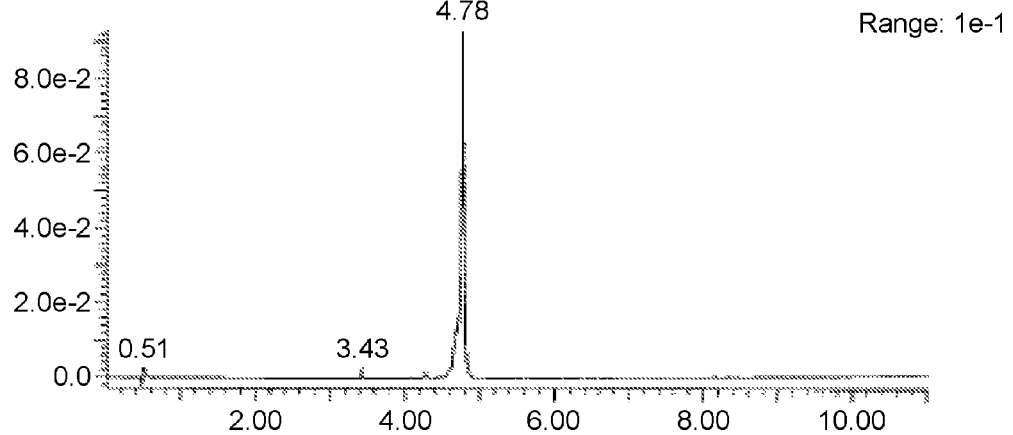
Figure 1:
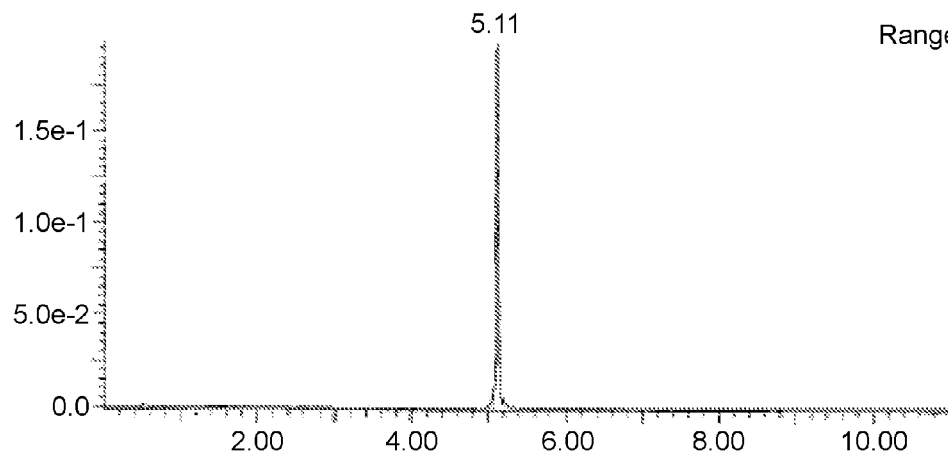

Hereafter, the present invention is described in greater detail.

1. Peptide Having 4 Linked CTL Epitopes

In the present invention, the "peptide having 4 linked CTL epitopes" means 4 peptides selected from among CTL epitope peptides derived from the same and/or different tumor antigen molecules linearly linked via linkers as a single molecule.

The "CTL epitope peptide derived from tumor antigen molecules" is a peptide resulting from decomposition of tumor antigens within tumor cells, and it is bound to the HLA class I molecule and presented on the cell surface. Thus, it is recognized by a tumor-specific CTL and/or it can induce and/or activate tumor-specific CTLs. "Induction of tumor-specific CTLs" refers to differentiation and/or proliferation of CTLs that specifically recognize CTL epitope peptides derived from tumor antigen molecules in vitro or in vivo. Further, "activation of tumor-specific CTL" refers to production of interferon-γ (IFN-γ) and/or exhibition of cytotoxic activity by means of release of cytotoxic substances or the like when CTL recognizes an antigen presented by the HLA class I molecule. The "CTL epitope peptide derived from a tumor antigen molecule" used herein is occasionally referred to as a "CTL epitope peptide."

As CTL epitope peptides derived from tumor antigen molecules, those shown below are known:

| | |
|---|---|
| PEP1: | (SEQ ID NO: 1 [WO 2001/011044])<br>KLVERLGAA; |
| PEP2: | (SEQ ID NO: 2 [WO 2002/010369])<br>ASLDSDPWV; |
| PEP3: | (SEQ ID NO: 3 [WO 2002/010369])<br>ALVEFEDVL; |
| PEP4: | (SEQ ID NO: 4 [WO 2000/12701])<br>LLQAEAPRL; |
| PEP5: | (SEQ ID NO: 5 [JP H11-318455 A (1999)])<br>DYSARWNEI; |
| PEP6: | (SEQ ID NO: 6 [WO 2000/12701])<br>VYDYNCHVDL; |
| PEP7: | (SEQ ID NO: 7 [JP 2000-000270 A])<br>LYAWEPSFL; |
| PEP8: | (SEQ ID NO: 8 [WO 2001/011044])<br>DYLRSVLEDF; |
| PEP9: | (SEQ ID NO: 9 [WO 2008/007711])<br>QIRPIFSNR; |
| PEP10: | (SEQ ID NO: 10 [WO 2009/022652])<br>ILEQSGEWWK; |
| PEP11: | (SEQ ID NO: 11 [WO 2009/022652])<br>VIQNLERGYR; |
| PEP12: | (SEQ ID NO: 12 [WO 1999/067288])<br>KLKHYGPGWV; |

PEP13: (SEQ ID NO: 13 [WO 2002/010369])
RLQEWCSVI;

PEP14: (SEQ ID NO: 14 [WO 2002/010369])
ILGELREKV;

PEP15: (SEQ ID NO: 15 [WO 2005/071075])
DYVREHKDNI;

PEP16: (SEQ ID NO: 16 [WO 2001/011044])
HYTNASDGL;

PEP17: (SEQ ID NO: 17 [JP 2000-000270 A])
NYSVRYRPGL;

PEP18: (SEQ ID NO: 18 [JP 2007-145715 A])
RYLTQETNKV;
and

PEP19: (SEQ ID NO: 19 [WO 2001/011044])
TFDYLRSVL.

PEP1, PEP2, PEP3, PEP4, PEP5, PEP8, PEP10, PEP12, PEP13, PEP14, and PEP15 are restricted by HLA-A2 and CTLs can then be induced and/or activated. PEP2, PEP5, PEP6, PEP7, PEP8, PEP12, PEP13, PEP15, PEP16, PEP17, PEP18, and PEP19 are restricted by HLA-A24 and CTLs can then be induced and/or activated. PEP1, PEP2, PEP4, PEP5, PEP6, PEP9, PEP10, PEP11, PEP12, PEP13, PEP15, and PEP16 are restricted by the HLA-A3 supertype and CTLs can then be induced and/or activated. In addition, PEP2 and PEP6 are restricted by HLA-A26 and CTLs can then be induced and/or activated. Expression of genes encoding such CTL epitope peptides is observed in a plurality of types of cancers (Yang, D. et al., Cancer Res., 1999, 59: 4056-63; Harashima, N. et al., Eur. J. Immunol., 2001, 31 (2), 323-32).

Various types of peptides having 4 linked CTL epitopes that are obtained by linearly linking 4 types of CTL epitope peptides selected from among particular 13 types of the CTL epitope peptides described above via linkers as a single molecule can serve as the "peptides having 4 linked CTL epitopes" according to the present invention. Three of more CTLs specific for relevant CTL epitope peptides can be induced and/or activated. Peptides that could not be directly evaluated in terms of CTL epitope-peptide-specific induction (i.e., PEP2 and PEP10) may be subjected to cleavage experiment with immunoproteasomes (Example 3), so as to determine the occurrence of epitope-peptide-specific CTL induction. In general, antigen proteins that are incorporated into antigen presenting cells are known to be cleaved with proteasomes or immunoproteasomes, and such procedure is known to be indispensable for the incorporated antigen proteins to present antigens mediated by HLA (e.g., Rock K. L., York, I. A., Goldberg, A. L., Nat. Immunol., 2004, 5(7): 670-677). It is necessary that CTL epitope peptides be cleaved at adequate sites, so as to allow such epitope peptides to bind to HLA pockets. It is necessary that C terminal amino acids of the CTL epitope peptides be determined as a result of cleavage with proteasomes or immunoproteasomes (Rock K. L., York, I. A., Goldberg, A. L., Nat. Immunol., 2004, 5(7): 670-677). It was presumed that CTL epitope peptides would be presented by dendritic cells when peptides having 4 linked epitopes were administered to humans. On the basis of such presumption, cleavage patterns of the peptides having 4 linked epitopes were analyzed in vitro using immunoproteasomes expressed in dendritic cells at high levels. When CTL epitope peptides appear as a result of cleavage with immunoproteasomes, it can be determined that CTL specific for such epitope peptides is induced.

In the present description, 4 types of CTL epitope peptides selected from among particular 13 types of the CTL epitope peptides are selected, optionally redundantly, from among the peptide as shown in SEQ ID NO: 1 (PEP1), the peptide as shown in SEQ ID NO: 2 (PEP2), the peptide as shown in SEQ ID NO: 4 (PEP4), the peptide as shown in SEQ ID NO: 5 (PEP5), the peptide as shown in SEQ ID NO: 6 (PEP6), the peptide as shown in SEQ ID NO: 7 (PEP7), the peptide as shown in SEQ ID NO: 8 (PEP8), the peptide as shown in SEQ ID NO: 9 (PEP9), the peptide as shown in SEQ ID NO: 10 (PEP10), the peptide as shown in SEQ ID NO: 13 (PEP13), the peptide as shown in SEQ ID NO: 15 (PEP15), the peptide as shown in SEQ ID NO: 17 (PEP17), and the peptide as shown in SEQ ID NO: 18 (PEP18).

In the present invention, a peptide having an amino acid sequence having substitution, insertion, deletion, and/or addition of one or a plurality of amino acids in the amino acid sequence of PEP1, PEP2, PEP4, PEP5, PEP6, PEP7, PEP8, PEP9, PEP10, PEP13, PEP15, PEP17, or PEP18 and having the capacity for inducing CTL and the capacity for inducting immunoglobulin productions equivalent to or higher than those of the original peptide can be used as a "CTL epitope peptide." The term "plurality" used herein refers to 1 to 3, and preferably 1 or 2. An example of such peptide is a peptide obtained by substitution of amino acids having properties similar to those of the original amino acid (i.e., a peptide obtained by conservative amino acid substitution).

The peptide having 4 linked CTL epitopes according to the present invention comprises 4 epitope peptides that are selected, optionally redundantly, from among PEP1, PEP2, PEP4, PEP5, PEP6, PEP7, PEP8, PEP9, PEP10, PEP13, PEP15, PEP17, and PEP18 linearly linked via linkers.

Any linker can be used, provided that it is cleaved upon administration of a peptide having 4 linked CTL epitopes to an organism, and the linked CTL epitope peptides can be separated from each other. Examples thereof include an ester bond, an ether bond, an amide bond, a sugar chain linker, a polyethylene glycol linker, and an amino acid linker. Examples of amino acid sequences used as amino acid linkers include an arginine dimer, an arginine trimer, an arginine tetramer, a lysine dimer, a lysine trimer, a lysine tetramer, a glycine dimer, a glycine trimer, a glycine tetramer, a glycine pentamer, a glycine hexamer, an alanine-alanine-tyrosine (AAY), isoleucine-leucine-alanine (ILA), and arginine-valine-lysine-arginine (RVKR), with an arginine dimer or trimer being preferable.

CTL epitope peptides to be selected and the arrangements thereof can be determined by administering a peptide having 4 linked epitopes obtained by synthesizing epitopes in given combinations and in a given order to human HLA-A transgenic mice and evaluating the occurrence of CTL epitope peptide specific CTL induction in vivo.

Preferably, the peptide having 4 linked epitopes according to the present invention has one or more features selected from the features (1) to (5) below:

(1) the peptide comprises PEP2 at the C terminus (except for the peptide comprising PEP7 and PEP8 at the N terminus successively disposed in such order from the N terminus via a linker);

(2) the peptide comprises PEP4 at the C terminus;

(3) the peptide comprises PEP10 at the C terminus;

(4) the peptide comprises PEP6 and PEP5 at the C terminus successively disposed in such order from the N terminus via a linker; and (5) the peptide comprises PEP5, PEP6, PEP9, and PEP18.

More preferably, the peptide having 4 linked epitopes according to the present invention has a feature selected from the features (1) to (5) below:

(1) the peptide comprises 3 CTL epitope peptides selected from among PEP1, PEP7, PEP8, and PEP13 and, at the C terminus, PEP2 (except for the peptide comprising PEP7 and PEP8 at the N terminus successively disposed in such order from the N terminus via a linker);

(2) the peptide comprises 3 CTL epitope peptides, PEP5, PEP6, and PEP9, and, at the C terminus, PEP4;

(3) the peptide comprises 3 CTL epitope peptides selected from among PEP1, PEP13, PEP15, PEP17, and PEP18 and, at the C terminus, PEP10;

(4) the peptide comprises 2 CTL epitope peptides, PEP1 and PEP7, and PEP6 and PEP5 at the C terminus successively disposed in such order from the N terminus via a linker; and (5) the peptide comprises 3 CTL epitope peptides, PEP5, PEP6, and PEP18, and, at the C terminus, PEP9.

Further preferably, the peptide having 4 linked epitopes according to the present invention comprises or consists of a sequence selected from among the following sequences, wherein "-(L)-" represents a linker:

PEP5-(L)-PEP6-(L)-PEP9-(L)-PEP4 (TPV01);
PEP9-(L)-PEP5-(L)-PEP6-(L)-PEP4 (TPV02);
PEP6-(L)-PEP5-(L)-PEP9-(L)-PEP4 (TPV03);
PEP6-(L)-PEP9-(L)-PEP5-(L)-PEP4 (TPVO4);
PEP9-(L)-PEP6-(L)-PEP5-(L)-PEP4 (TPV05);
PEP5-(L)-PEP9-(L)-PEP6-(L)-PEP4 (TPV06);
PEP1-(L)-PEP7-(L)-PEP8-(L)-PEP2 (TPV07);
PEP1-(L)-PEP8-(L)-PEP7-(L)-PEP2 (TPV08);
PEP7-(L)-PEP1-(L)-PEP8-(L)-PEP2 (TPV09);
PEP8-(L)-PEP7-(L)-PEP1-(L)-PEP2 (TPV10);
PEP8-(L)-PEP1-(L)-PEP7-(L)-PEP2 (TPV11);
PEP7-(L)-PEP13-(L)-PEP8-(L)-PEP2 (TPV12);
PEP8-(L)-PEP13-(L)-PEP7-(L)-PEP2 (TPV13);
PEP13-(L)-PEP7-(L)-PEP8-(L)-PEP2 (TPV14);
PEP8-(L)-PEP7-(L)-PEP13-(L)-PEP2 (TPV15);
PEP13-(L)-PEP8-(L)-PEP7-(L)-PEP2 (TPV16);
PEP13-(L)-PEP15-(L)-PEP18-(L)-PEP10 (TPV17);
PEP13-(L)-PEP18-(L)-PEP15-(L)-PEP10 (TPV18);
PEP15-(L)-PEP13-(L)-PEP18-(L)-PEP10 (TPV19);
PEP15-(L)-PEP18-(L)-PEP13-(L)-PEP10 (TPV20);
PEP18-(L)-PEP13-(L)-PEP15-(L)-PEP10 (TPV21);
PEP18-(L)-PEP15-(L)-PEP13-(L)-PEP10 (TPV22);
PEP1-(L)-PEP15-(L)-PEP18-(L)-PEP10 (TPV23);
PEP1-(L)-PEP18-(L)-PEP15-(L)-PEP10 (TPV24);
PEP15-(L)-PEP1-(L)-PEP18-(L)-PEP10 (TPV25);
PEP15-(L)-PEP18-(L)-PEP1-(L)-PEP10 (TPV26);
PEP18-(L)-PEP1-(L)-PEP15-(L)-PEP10 (TPV27);
PEP18-(L)-PEP15-(L)-PEP1-(L)-PEP10 (TPV28);
PEP15-(L)-PEP17-(L)-PEP13-(L)-PEP10 (TPV29);
PEP15-(L)-PEP13-(L)-PEP17-(L)-PEP10 (TPV30);
PEP17-(L)-PEP15-(L)-PEP13-(L)-PEP10 (TPV31);
PEP17-(L)-PEP13-(L)-PEP15-(L)-PEP10 (TPV32);
PEP13-(L)-PEP17-(L)-PEP15-(L)-PEP10 (TPV33);
PEP13-(L)-PEP15-(L)-PEP17-(L)-PEP10 (TPV34);
PEP6-(L)-PEP18-(L)-PEP5-(L)-PEP9 (TPV35);
PEP6-(L)-PEP5-(L)-PEP18-(L)-PEP9 (TPV36);
PEP1-(L)-PEP7-(L)-PEP6-(L)-PEP5 (TPV37); and
PEP7-(L)-PEP1-(L)-PEP6-(L)-PEP5 (TPV38).

The peptide having 4 linked CTL epitopes according to the present invention can further comprise a peptide sequence consisting of hydrophilic amino acids. Such peptide sequence can be added to the N terminus and/or the C terminus of the peptide having 4 linked CTL epitopes, and it is preferably added to the N terminus. Such peptide sequence consists of 1 to 15, preferably 2 to 10, and more preferably 3 to 5 hydrophilic amino acids selected from the group consisting of arginine, histidine, lysine, threonine, tyrosine, serine, asparagine, glutamine, aspartic acid, and glutamic acid. For example, an arginine trimer (RRR) or arginine tetramer (RRRR) can be used as such peptide sequence. Examples of peptides having 4 linked CTL epitopes comprising such peptide sequences added thereto include RRR-TPV06, RRRR-TPV06, TPV06-RRR, TPV06-RRRR, RRR-TPV10, RRRR-TPV10, TPV10-RRR, TPV10-RRRR, RRR-TPV12, RRRR-TPV12, TPV12-RRR, TPV12-RRRR, RRR-TPV21, RRRR-TPV21, TPV21-RRR, TPV21-RRRR, RRR-TPV26, RRRR-TPV26, TPV26-RRR, TPV26-RRRR, RRR-TPV30, RRRR-TPV30, TPV30-RRR, TPV30-RRRR, KKK-TPV06, KKKK-TPV06, TPV06-KKK, TPV06-KKKK, KKK-TPV10, KKKK-TPV10, TPV10-KKK, TPV10-KKKK, KKK-TPV12, KKKK-TPV12, TPV12-KKK, TPV12-KKKK, KKK-TPV21, KKKK-TPV21, TPV21-KKK, TPV21-KKKK, KKK-TPV26, KKKK-TPV26, TPV26-KKK, TPV26-KKKK, KKK-TPV30, KKKK-TPV30, TPV30-KKK, TPV30-KKKK, HHH-TPV06, HHHH-TPV06, TPV06-HHH, TPV06-HHHH, HHH-TPV10, HHHH-TPV10, TPV10-HHH, TPV10-HHHH, HHH-TPV12, HHHH-TPV12, TPV12-HHH, TPV12-HHHH, HHH-TPV21, HHHH-TPV21, TPV21-HHH, TPV21-HHHH, HHH-TPV26, HHHH-TPV26, TPV26-HHH, TPV26-HHHH, HHH-TPV30, HHHH-TPV30, TPV30-HHH, TPV30-HHHH, RRKK-TPV12, RKRK-TPV12, RHRH-TPV12, RRHH-TPV12, KKHH-TPV12, and KHKH-TPV12, with KKK-TPV06, KKKK-TPV06, KKK-TPV10, KKKK-TPV10, KKK-TPV12, KKKK-TPV12, KKK-TPV21, KKKK-TPV21, KKK-TPV26, KKKK-TPV26, KKK-TPV30, KKKK-TPV30, HHH-TPV06, HHHH-TPV06, HHH-TPV10, HHHH-TPV10, HHH-TPV12, HHHH-TPV12, HHH-TPV21, HHHH-TPV21, HHH-TPV26, HHHH-TPV26, HHH-TPV30, HHHH-TPV30, RRKK-TPV12, RKRK-TPV12, RHRH-TPV12, RRHH-TPV12, KKHH-TPV12, and KHKH-TPV12 being preferable, and RRR-TPV06, RRRR-TPV06, RRR-TPV10, RRRR-TPV10, RRR-TPV12, RRRR-TPV12, TRRR-TPV21, RRRR-TPV21, RRR-TPV26, RRRR-TPV26, RRR-TPV30, and RRRR-TPV30 being more preferable. A peptide comprising such peptide sequence is known to have improved solubility in an aqueous solvent (Abdelkrim Alileche et al., Peptides 38, 2012, 302-311; JP 2006-188507 A). With the addition of such peptide sequence to the peptide having 4 linked CTL epitopes according to the present invention, a degree of solubility of the peptide having 4 linked CTL epitopes in an aqueous solvent can be improved.

In the peptide having 4 linked epitopes according to the present invention, CTL epitope peptide specific CTLs can be induced and/or activated in at least three types, and preferably four types of CTL epitope peptides of the 4 linked types of CTL epitope peptides. In addition, production of an immunoglobulin specific for each CTL epitope peptide can be induced. In the present invention, the term "immunoglobulins" refers to IgG, IgM, IgA, or IgD.

The peptide having 4 linked epitopes according to the present invention may be an acid addition salt or a base addition salt. Examples of acids that are generally used to form acid addition salts include organic acids, such as hydrochloric acid, hydrobromic acid, hydriodic acid, oxalic acid, p-bromophenyl sulfonic acid, carboxylic acid, succinic acid, citric acid, benzoic acid, acetic acid, and trifluoroacetic acid. Examples of base addition salts include salts induced from inorganic bases, such as ammonium hydroxide, alkali hydroxide, alkaline-earth metal hydroxide, carbonate, and bicarbonate.

2. Production of a Peptide Having 4 Linked CTL Epitopes

The peptide having 4 linked CTL epitopes according to the present invention can be produced by common techniques, for example, peptide synthesis, such as liquid-phase synthesis or solid-phase synthesis, or peptide synthesis involving the use of an automated peptide synthesizer (Kelley et al., Genetics Engineering Principles and Methods, Setlow, J. K. eds., Plenum Press NY., 1990, Vol. 12, pp. 1-19; Stewart et al., Solid-Phase Peptide Synthesis, 1989, W. H. Freeman Co.; Houghten, Proc. Natl. Acad. Sci., U.S.A., 1985, 82: p. 5132, "Shin Seikagaku Jikken Kouza (New Biochemical Experiment) 1, Protein IV, 1992, the Japanese Biochemical Society (ed.), Tokyo Kagaku Doujin). Peptide synthesis is carried out by preparing amino acids in which functional groups other than α-amino groups and α-carboxyl groups to be bound of the amino acids are protected and forming peptide bonds between α-amino groups and α-carboxyl groups of the amino acids. In general, a carboxyl group of an amino acid residue located at the C terminus of a peptide is bound to a solid phase via an adequate spacer or linker. A protective group at the amino terminus of the dipeptide obtained above is selectively removed and a peptide bond is formed between the amino terminus and the α-carboxyl group of the subsequent amino acid residue. This procedure is continued to produce a peptide with a protected side group, and all protective groups are removed and separated from the solid phase at the end. Protective group types, methods for protecting the same, and methods of peptide binding are described in detail in the documents mentioned above.

Alternatively, a peptide may be produced via genetic recombination, phage display, or other techniques with the use of a nucleic acid encoding the peptide having 4 linked epitopes according to the present invention.

A genetic recombination technique comprises inserting DNA encoding the peptide having 4 linked epitopes according to the present invention into an adequate expression vector, introducing the vector into adequate host cells, culturing the cells, and recovering the target peptides from the cells or the extracellular fluid. Examples of vectors include, but are not limited to, plasmid, phage, cosmid, phagemid, and virus vectors. Vectors are introduced into host cells, such as bacterial host cells (e.g., *E. coli* and *Bacillus subtilis*), yeast cells, insect cells, animal cells (e.g., mammalian cells), and plant cells. Transformation or transfection into such cells is carried out via, for example, the calcium phosphate method, electroporation, lipofection, the particle gun method, or the PEG method. Transformed cells are cultured in accordance with a conventional technique for host organism culture. In order to facilitate recovery of the peptide according to the present invention, it is preferable that a peptide generated via expression be secreted extracellularly. To this end, DNA encoding a peptide sequence that enables peptide secretion from the cells is bound to the 5' terminal side of DNA encoding a target peptide. Alternatively, a target peptide accumulated in the cells can be recovered. In such a case, cells are physically or chemically broken and a target peptide is recovered via a protein purification technique.

The peptide thus obtained can be recovered or purified via a conventional technique, for example, chromatography techniques, such as gel filtration chromatography, ion exchange column chromatography, affinity chromatography, reverse phase column chromatography, or HPLC, ammonium sulfate fractionation, ultrafiltration, or immunoadsorption.

3. Cytotoxic T Lymphocytes

With the use of the peptide having 4 linked epitopes according to the present invention, CTL epitope peptide specific CTLs that damage cancer cells can be obtained in vitro and/or ex vivo. A method for inducing CTL using a CTL epitope peptide in vitro and/or ex vivo is known (e.g., JP 2006-14637 A), and such technique can be employed in the present invention. For example, plate adhesion cells in the peripheral blood mononuclear cells (PBMCs) derived from healthy individuals or cancer patients are cultured in the presence of cytokines, such as GM-CSF or IL-4, so as to induce dendritic cells (DCs). After the dendritic cells have been pulsed with the peptide having 4 linked epitopes according to the present invention, x-rays are applied thereto, so as to prepare antigen-presenting cells (stimulators). When DCs cannot be used, the peripheral blood mononuclear cells (PBMCs) derived from healthy individuals or the same cancer patients may be pulsed with the peptide having 4 linked epitopes according to the present invention, x-rays may be applied thereto, and the resultants may be used. Subsequently, peripheral blood mononuclear cells (PBMCs) derived from healthy individuals or peripheral blood mononuclear cells (PBMCs) derived from cancer patients or lymphocytes in the relevant lymph nodes (i.e., responders) are added and then cultured in the presence of cytokines, such as IL-2, IL-4, or IL-7. Thereafter, the antigen presenting cells obtained via pulsing described above are stimulated again with the addition of the peptide having 4 linked epitopes according to the present invention and further cultured in the presence of cytokines, such as IL-2.

Any medium in which T lymphocytes can survive may be used as a cell culture medium used for CTL induction. For example, a medium prepared by adding various cytokines (e.g., IL-2) and fetal calf serum (FCS) to RHAMα medium (LAK medium described in Kawai, K., Sasaki, T., Saijo-Kurita, K., Akaza, H., Koiso, K., and Ohno, T., Cancer Immunol. Immunother., 35, 225-229, 1992), AIMV medium (GIBCO BRL, Life Technologies, INC.), or RPMI 1640 medium can be used.

Culture may be conducted under conditions well known in the art. For example, culture temperature is at 33° C. to 41° C., and preferably 37° C. An inert gas containing air or oxygen of adequate concentration and carbon dioxide of adequate concentration (e.g., 5% $CO_2$) to adjust the pH of the medium to about 7.4 can be used as a gas phase. Culture is preferably conducted for 4 to 10 days, and more preferably 7 days or 8 days. Some CTLs induced via such culture are CTL epitope peptide specific for each of at least three types, and preferably four types of CTL epitope peptides among the four types of CTL epitope peptides constituting the peptide having 4 linked epitopes, and thus they can specifically damage cancer cells.

4. Pharmaceutical Composition

The peptide having 4 linked epitopes according to the present invention can be used as an active ingredient of a pharmaceutical composition used for cancer immunotherapy.

The pharmaceutical composition according to the present invention can contain, as an active ingredient(s), one or more of the peptides having 4 linked epitopes. By including a plurality of the peptides having 4 linked epitopes, stronger effects can be expected. In addition, the resulting pharmaceutical composition can exert higher versatility, so that it can be administered as a peptide vaccine for cancer to a wider range of cancer patients, regardless of the HLA types of patients.

Genes encoding PEP1, PEP2, PEP4, PEP5, PEP6, PEP7, PEP8, PEP9, PEP10, PEP13, PEP15, PEP17, and PEP18 included in the peptide having 4 linked epitopes according to the present invention are observed to be expressed in a plurality of types of solid cancers and blood cancers. Examples of solid cancers include brain tumor, lung cancer, breast cancer, thyroid cancer, uterine cervix cancer, cancer of uterine body, ovarian cancer, esophageal cancer, gastric cancer, gastrointestinal stromal tumor (GIST), pancreatic cancer, colon cancer, rectal cancer, anal cancer, renal cancer, liver cancer, biliary tract cancer, head and neck cancer, bladder cancer, prostate cancer, malignant melanoma, skin cancer, lingual cancer, osteosarcoma, chondrosarcoma, fibrosarcoma, liposarcoma, angiosarcoma, rhabdomyoblastoma, and leiomyosarcoma. Examples of blood cancers include leukemia, malignant lymphoma, and myeloma. Accordingly, the peptide having 4 linked epitopes according to the present invention is useful for the treatment and/or prevention of such cancers. The term "treatment and/or prevention of cancer" used herein refers to prevention of the development/recurrence of cancer, suppression of the progression/exacerbation of cancer, or the improvement of cancer conditions.

The pharmaceutical composition according to the present invention can contain pharmaceutically acceptable materials, such as various common organic or inorganic carriers. Examples of pharmaceutical carriers that can be used include stabilizers, antibacterials, buffers, isotonizing agents, chelating agents, pH adjusters, surfactants, fillers, thickeners, binders, humectants, disintegrators, surface active agents, lubricants, soothing agents, diluents, and excipients that are generally used in accordance with the form of administration of relevant pharmaceutical preparations. Pharmaceutical preparations are preferably prepared in the form of formulations supplemented with such carriers in accordance with conventional techniques.

The pharmaceutical composition according to the present invention can contain an adjuvant that is known to be used at the time of vaccine administration. Examples of adjuvants include Complete Freund's adjuvant (CFA), Incomplete Freund's adjuvant (IFA), alum, lipid A, monophosphoryl lipid A, bacterial preparations such as BCG (*Bacillus*-Calmette-Guerrin), nucleic acids such as CpG-DNA and dsRNA, preparations of bacterial components such as tuberculin, naturally-occurring polymers, such as keyhole limpet hemocyanin and yeast mannan, muramyl-tripeptide, muramyl-dipeptide, or a derivative of either thereof, alum, nonionic block copolymers, and cytokines such as interleukin 2 (IL-2), granulocyte macrophage colony stimulating factor (GM-CSF), interferon-α (IFN-α), and interferon-β (IFN-β). These adjuvants can be used alone or in combinations of two or more. Adjuvants may be administered simultaneously with the pharmaceutical composition according to the present invention in the form of a mixture or as an emulsion.

In addition to the peptide having 4 linked epitopes, the pharmaceutical composition according to the present invention may comprise one or more of a known CTL epitope peptide derived from tumor antigen molecules, a peptide containing the same, or a peptide comprising the CTL epitope peptides linked to each other (hereafter, referred to as "known CTL epitope peptides derived from tumor antigen molecules"). Examples of known CTL epitope peptides derived from tumor antigen molecules include, but are not limited to, WT-1 p126-134, modified (M236Y) WT-1 p235-243, NY-ESO-1 p157-165, modified (T210M) gp100 p209-217, survivin-2B p80-88, Her-2/neu p63-71, VEGFR2 p169-177, MART-1 p26-35, Glypican-3 p298-306, and SPARC p143-151. In this case, the peptide having 4 linked epitopes according to the present invention and the known CTL epitope peptides derived from tumor antigen molecules may be prepared in the form of a single-agent preparation. Alternatively, a preparation comprising, as an active ingredient, the peptide having 4 linked epitopes according to the present invention may be separated from a preparation comprising, as an active ingredient, the known CTL epitope peptides derived from tumor antigen molecules.

The dosage form of the pharmaceutical composition according to the present invention can be selected in accordance with the form of administration. Representative examples of dosage forms include, but are not limited to, liquid preparations, emulsions, liposome preparations, lipid emulsions, cyclodextrin inclusion complexes, suspensions, ointments, creams, transdermally absorbed agents, transmucosally absorbed agents, tablets, pills, capsules, powders, powdered drugs, granules, fine grains, and syrups. In accordance with the route of administration, such dosage forms are further classified as, for example, oral preparations, parenteral preparations, transnasal preparations, transvaginal preparations, suppositories, sublingual formulations, inhalants, eye drops, or ear drops, and such preparations can be combined, molded, or prepared in accordance with conventional techniques. In addition to the application in the form of liquid preparations, such preparation can be subjected to lyophilization, so as to make the pharmaceutical preparation storable. When such pharmaceutical preparation is to be used, it may be dissolved with the aid of, for example, a buffer containing water and physiological saline, so as to adjust the concentration thereof to an adequate level.

The pharmaceutical composition according to the present invention may comprise, as an active ingredient, CTLs induced in vitro and/or ex vivo with the use of the peptide having 4 linked epitopes according to the present invention. Such pharmaceutical composition is preferably in the form of a parenteral agent.

5. Treatment Method

The pharmaceutical composition according to the present invention can be administered to a wide range of cancer patients, such as patients who are positive for HLA types selected from the group consisting of HLA-A2, HLA-A24, HLA-A26, and HLA-A3 supertype, and treatment can be initiated without conducting HLA typing prior to the treatment.

When the pharmaceutical composition according to the present invention is administered to a cancer patient, CTLs specific for at least three, and preferably four types of CTL epitope peptides constituting the peptide having 4 linked epitopes as an active ingredient of the pharmaceutical composition can be induced and/or activated. In addition, production of immunoglobulins specific for relevant CTL epitope peptides can be induced. The level of induction of immunoglobulin production upon administration of the peptide having 4 linked epitopes as an active ingredient is significantly higher than the level of induction of immunoglobulin production observed upon administration of a mixture of CTL epitope peptides that are to be contained in the peptide having 4 linked epitopes but are not linked to each other. Accordingly, the peptide having 4 linked epitopes according to the present invention can effectively treat and/or prevent cancer in a cancer patient.

The pharmaceutical composition according to the present invention can be administered via, for example, oral administration, intravenous administration, intraarterial administration, intramuscular administration, subcutaneous administration, intracutaneous administration, sublingual administration, intraperitoneal administration, intrarectal administration, transdermal administration, transmucosal administration, transnasal administration, transvaginal administration, transocular administration, or aspiration. When preparations comprising, as active ingredients, a plurality of peptides having 4 linked epitopes or known CTL epitope peptides derived from tumor antigen molecules are prepared in the form of separate pharmaceutical compositions, such pharmaceutical compositions can be administered simultaneously or non-simultaneously via the same route or via separate routes.

Dosage of the pharmaceutical composition according to the present invention can be adequately adjusted in accordance with factors such as the conditions/severity of cancer to be treated, the age of the patient, or the body weight of the patient. For example, a pharmaceutical composition containing the peptide having 4 linked epitopes in an amount of 0.0001 mg to 1000 mg, preferably 0.001 mg to 100 mg, and further preferably 0.01 mg to 50 mg, may be repeatedly administered once every several days, several weeks, or several months. When the pharmaceutical composition according to the present invention comprises, as active ingredients, CTLs induced in vitro and/or ex vivo with the use of the peptide having 4 linked epitopes according to the present invention, it is preferable that $2 \times 10^6$ to $2 \times 10^8$ CTLs be administered per kg of the body weight every day at intervals of 1 to 2 weeks.

The pharmaceutical composition according to the present invention can be administered to a cancer patient in combination with pharmaceutical products that are generally used for cancer chemotherapy. Examples of such pharmaceutical products include: alkylating agents, such as cyclophosphamide, temozolomide, and bendamustine; antimetabolites, such as tegafur-uracil, tegafur-gimeracil-oteracil potassium, methotrexate, and gemcitabine; platinum-containing drugs, such as cisplatin and oxaliplatin; plant alkaloid preparations, such as irinotecan, eribulin, paclitaxel, docetaxel, and vincristine; carcinostatic antibiotics, such as doxorubicin, bleomycin, and actinomycin D; molecular-targeted drugs, such as imatinib, sunitinib, gefitinib, sorafenib, everolimus, trastuzumab, bevacizumab, rituximab, cetuximab, panitumumab, and mogamulizumab; hormonal therapy agents, such as bicalutamide, estramustine, and exemestane; and immunostimulatory agents, such as lenthinan, Picibanil, and Krestin. Such pharmaceutical products can be administered simultaneously or non-simultaneously with the pharmaceutical composition according to the present invention via the same route or via separate routes.

Hereafter, the present invention is described in greater detail with reference to the examples, although the present invention is not limited to these examples.

EXAMPLES

Example 1: Peptide Synthesis and Purification

Figure 2:
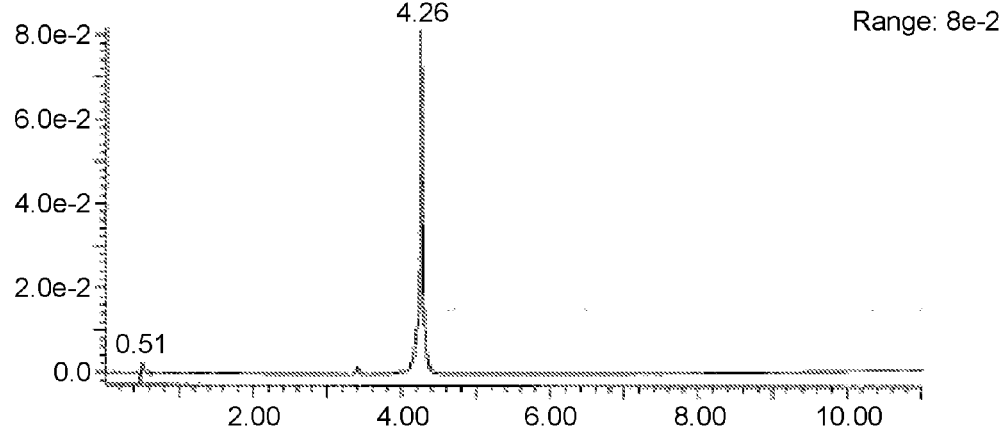
Figures 1, 2, 3, 4, 5, 6, 7:
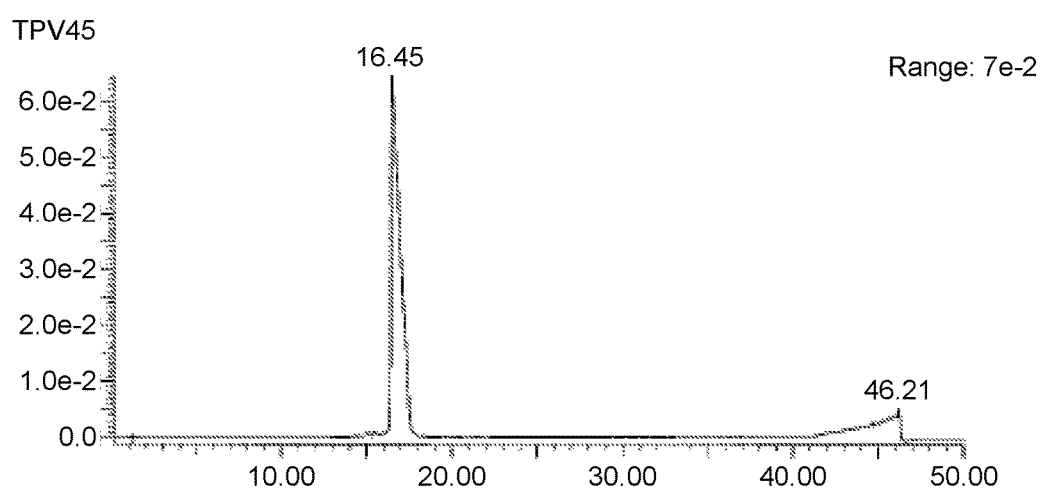
Figure 2:
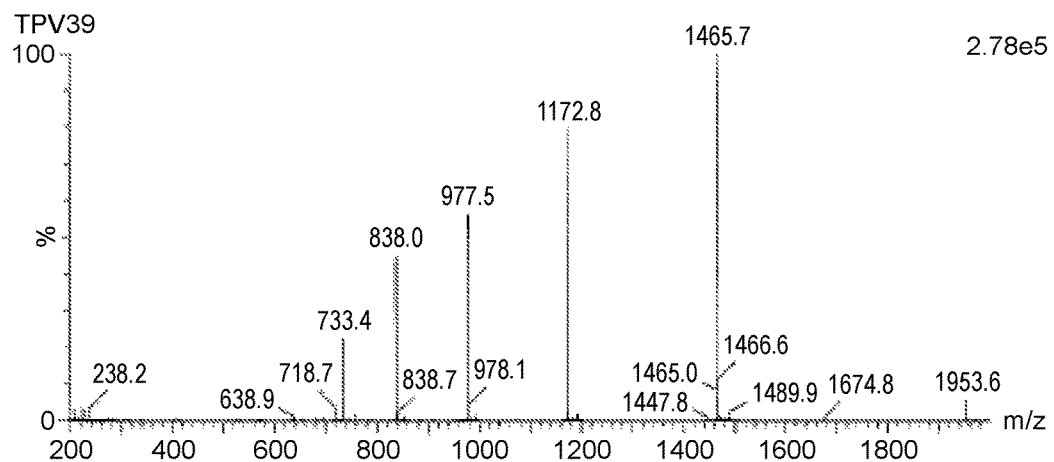
Figure 1:
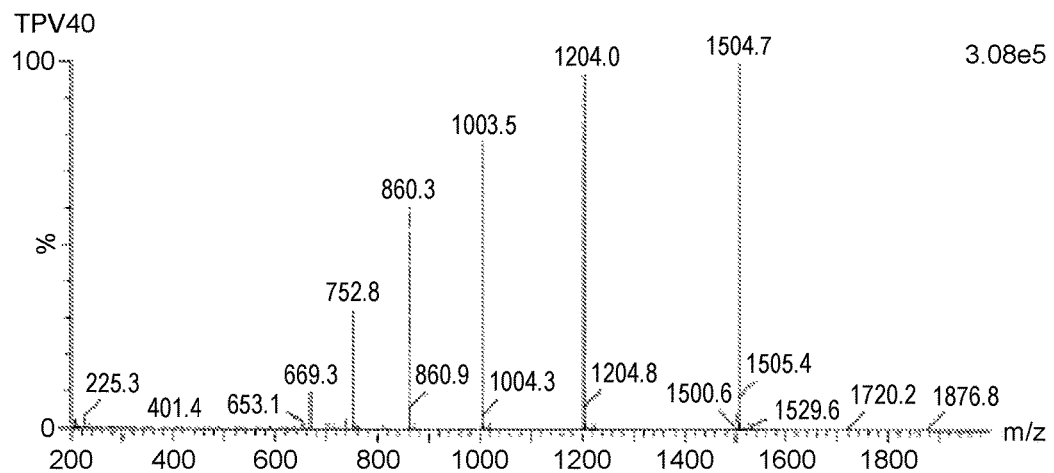
Figure 2:
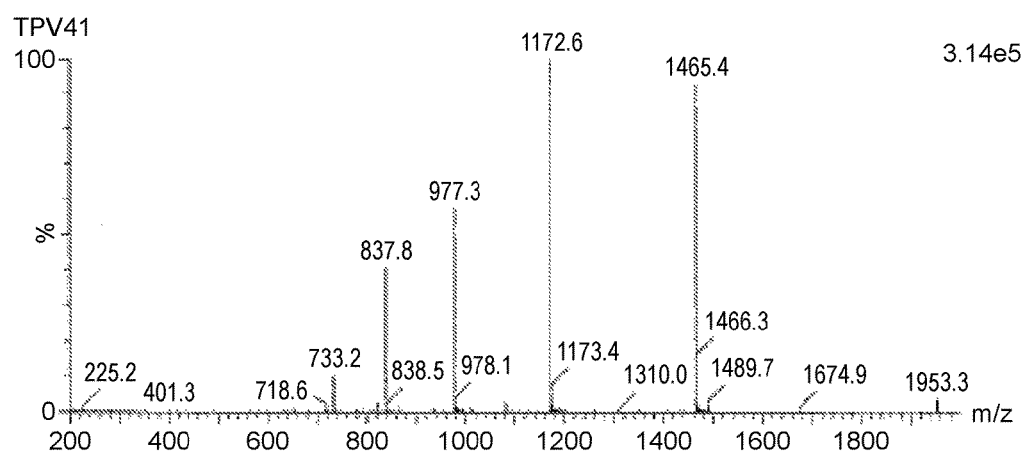
Figure 2:
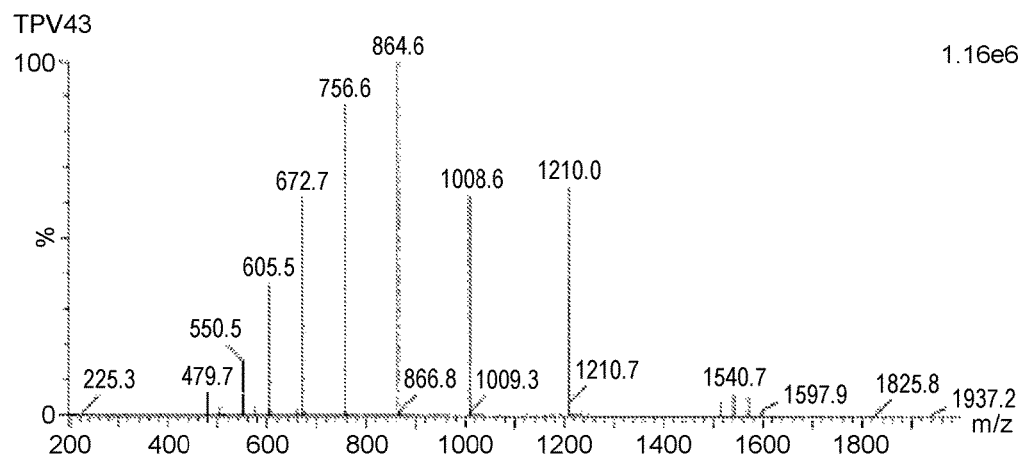
Figures 2, 3:
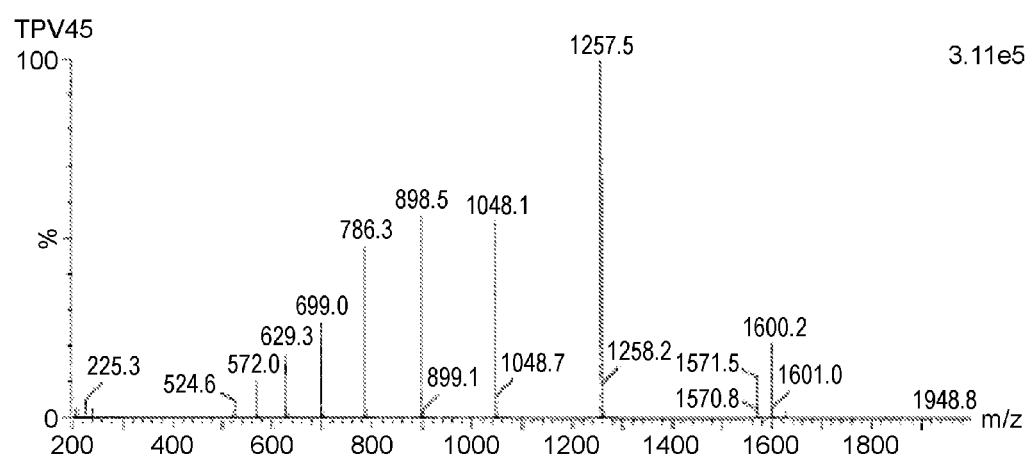

The CTL epitope peptides and the peptides having 4 linked epitopes were synthesized using a commercially available peptide synthesizer (Prelude, Protein Technologies, Inc.) by the solid-phase synthesis (Fmoc) method. Specifically, Alko-PEG resin was allowed to adsorb amino acids with protected active groups, a deblocking solution was injected thereinto, so as to remove protective groups, amino acids with protected active groups were injected thereinto, and they were allowed to react with each other, so as to synthesize dipeptides. By repeating such procedure, peptides comprising sequences of interest were synthesized. Peptide protective groups were removed by conducting a reaction in a deprotective solution containing 2.5% triisopropylsilane, 2.5% water, and 95% trifluoroacetic acid for 2 hours. With the addition of cold ether to the resulting filtrate, peptides were recovered in the form of precipitates. The resulting various synthetic peptides were purified using the YMC-Pack Pro C18 column (YMC Co., Ltd.) and the HPLC system (Gilson) with an aqueous solution of 0.1% TFA and acetonitrile as a mobile phase. After the final process of purification, the purity and the molecular weight of the peptides were analyzed by the LC-MS systems (Waters Acquity UPLC system, micromass ZQ). The peptides were lyophilized, stored at cool temperature in the dark, and then subjected to the examples described below. Tables 1-1 to 1-8 show the MS spectral data of the peptides having 4 linked epitopes (TPV01 to TPV45). FIGS. 1-1 to 1-7 show the LC data of TPV06, TPV10, TPV12, TPV21, TPV26, TPV30, TPV35, TPV37, TPV39, TPV40, TPV41, TPV43, and TPV45. FIGS. 2-1 to 2-3 shows the MS data of TPV39, TPV40, TPV41, TPV43, and TPV45.

TABLE 1-1

| Peptide | Molecular weight | Calculated | | Measured | |
|---|---|---|---|---|---|
| TPV01 | 5417.1 | $4H^+$ion | 1355.5 | $4H^+$ion | 1355.8 |
| | | $5H^+$ion | 1084.4 | $5H^+$ion | 1084.9 |
| | | $6H^+$ion | 903.8 | $6H^+$ion | 904.1 |
| | | $7H^+$ion | 774.9 | $7H^+$ion | ND |
| | | $8H^+$ion | 678.1 | $8H^+$ion | 678.3 |
| TPV02 | | $4H^+$ion | 1355.5 | $4H^+$ion | 1355.5 |
| | | $5H^+$ion | 1084.4 | $5H^+$ion | 1084.3 |
| | | $6H^+$ion | 903.8 | $6H^+$ion | 904.1 |
| | | $7H^+$ion | 774.9 | $7H^+$ion | 775.2 |
| | | $8H^+$ion | 678.1 | $8H^+$ion | ND |
| TPV03 | | $4H^+$ion | 1355.5 | $4H^+$ion | 1355.9 |
| | | $5H^+$ion | 1084.4 | $5H^+$ion | 1084.7 |
| | | $6H^+$ion | 903.8 | $6H^+$ion | 904.2 |
| | | $7H^+$ion | 774.9 | $7H^+$ion | 775.2 |
| | | $8H^+$ion | 678.1 | $8H^+$ion | 678.2 |
| TPV04 | | $4H^+$ion | 1355.5 | $4H^+$ion | 1355.6 |
| | | $5H^+$ion | 1084.4 | $5H^+$ion | 1084.5 |
| | | $6H^+$ion | 903.8 | $6H^+$ion | 904.2 |
| | | $7H^+$ion | 774.9 | $7H^+$ion | 775.0 |
| | | $8H^+$ion | 678.1 | $8H^+$ion | 678.8 |
| TPV05 | | $4H^+$ion | 1355.5 | $4H^+$ion | 1355.7 |
| | | $5H^+$ion | 1084.4 | $5H^+$ion | 1084.7 |
| | | $6H^+$ion | 903.8 | $6H^+$ion | 904.2 |
| | | $7H^+$ion | 774.9 | $7H^+$ion | 775.1 |
| | | $8H^+$ion | 678.1 | $8H^+$ion | 678.4 |
| TPV06 | | $4H^+$ion | 1355.5 | $4H^+$ion | 1354.4 |
| | | $5H^+$ion | 1084.4 | $5H^+$ion | 1084.2 |
| | | $6H^+$ion | 903.8 | $6H^+$ion | 903.5 |
| | | $7H^+$ion | 774.9 | $7H^+$ion | 774.6 |
| | | $8H^+$ion | 678.1 | $8H^+$ion | ND |

TABLE 1-2

| TPV07 | 5209.9 | $4H^+$ion | 1303.5 | $4H^+$ion | 1304.3 |
|---|---|---|---|---|---|
| | | $5H^+$ion | 1043.0 | $5H^+$ion | 1043.3 |
| | | $6H^+$ion | 869.3 | $6H^+$ion | 869.8 |
| | | $7H^+$ion | 745.3 | $7H^+$ion | 745.7 |
| | | $8H^+$ion | 652.2 | $8H^+$ion | 652.5 |
| TPV08 | | $4H^+$ion | 1303.5 | $4H^+$ion | 1303.8 |
| | | $5H^+$ion | 1043.0 | $5H^+$ion | 1043.5 |
| | | $6H^+$ion | 869.3 | $6H^+$ion | 870.2 |

TABLE 1-2-continued

|       |        |        |        |        |
|-------|--------|--------|--------|--------|
|       | 7H+ion | 745.3  | 7H+ion | 745.2  |
|       | 8H+ion | 652.2  | 8H+ion | 649.5  |
| TPV09 | 4H+ion | 1303.5 | 4H+ion | 1304.1 |
|       | 5H+ion | 1043.0 | 5H+ion | 1043.5 |
|       | 6H+ion | 869.3  | 6H+ion | 869.8  |
|       | 7H+ion | 745.3  | 7H+ion | 745.5  |
|       | 8H+ion | 652.2  | 8H+ion | 652.7  |
| TPV10 | 4H+ion | 1303.5 | 4H+ion | 1304.0 |
|       | 5H+ion | 1043.0 | 5H+ion | 1043.4 |
|       | 6H+ion | 869.3  | 6H+ion | 869.6  |
|       | 7H+ion | 745.3  | 7H+ion | 745.7  |
|       | 8H+ion | 652.2  | 8H+ion | 670.7  |
| TPV11 | 4H+ion | 1303.5 | 4H+ion | 1304.1 |
|       | 5H+ion | 1043.0 | 5H+ion | 1043.4 |
|       | 6H+ion | 869.3  | 6H+ion | 869.7  |
|       | 7H+ion | 745.3  | 7H+ion | 745.6  |
|       | 8H+ion | 652.2  | 8H+ion | 652.6  |

TABLE 1-3

|       |        |        |        |        |        |
|-------|--------|--------|--------|--------|--------|
| TPV12 | 5387.1 | 4H+ion | 1347.8 | 4H+ion | 1347.6 |
|       |        | 5H+ion | 1087.4 | 5H+ion | 1078.1 |
|       |        | 6H+ion | 898.9  | 6H+ion | 898.7  |
|       |        | 7H+ion | 770.6  | 7H+ion | 770.2  |
|       |        | 8H+ion | 674.4  | 8H+ion | ND     |
| TPV13 |        | 4H+ion | 1347.8 | 4H+ion | 1348.5 |
|       |        | 5H+ion | 1087.4 | 5H+ion | 1079.1 |
|       |        | 6H+ion | 898.9  | 6H+ion | 899.3  |
|       |        | 7H+ion | 770.6  | 7H+ion | 771.6  |
|       |        | 8H+ion | 674.4  | 8H+ion | 674.1  |
| TPV14 |        | 4H+ion | 1347.8 | 4H+ion | 1348.5 |
|       |        | 5H+ion | 1087.4 | 5H+ion | 1079.1 |
|       |        | 6H+ion | 898.9  | 6H+ion | 899.5  |
|       |        | 7H+ion | 770.6  | 7H+ion | 770.9  |
|       |        | 8H+ion | 674.4  | 8H+ion | 674.7  |
| TPV15 |        | 4H+ion | 1347.8 | 4H+ion | 1349.1 |
|       |        | 5H+ion | 1087.4 | 5H+ion | 1079.0 |
|       |        | 6H+ion | 898.9  | 6H+ion | 899.3  |
|       |        | 7H+ion | 770.6  | 7H+ion | 771.2  |
|       |        | 8H+ion | 674.4  | 8H+ion | 677.0  |
| TPV16 |        | 4H+ion | 1347.8 | 4H+ion | 1348.6 |
|       |        | 5H+ion | 1087.4 | 5H+ion | 1079.8 |
|       |        | 6H+ion | 898.9  | 6H+ion | 899.7  |
|       |        | 7H+ion | 770.6  | 7H+ion | ND     |
|       |        | 8H+ion | 674.4  | 8H+ion | ND     |

TABLE 1-4

|       |        |        |        |        |        |
|-------|--------|--------|--------|--------|--------|
| TPV17 | 5831.6 | 4H+ion | 1458.9 | 4H+ion | ND     |
|       |        | 5H+ion | 1167.3 | 5H+ion | 1168.1 |
|       |        | 6H+ion | 972.9  | 6H+ion | 973.9  |
|       |        | 7H+ion | 834.1  | 7H+ion | 834.3  |
|       |        | 8H+ion | 730.0  | 8H+ion | 730.3  |
| TPV18 |        | 4H+ion | 1458.9 | 4H+ion | ND     |
|       |        | 5H+ion | 1167.3 | 5H+ion | 1168.3 |
|       |        | 6H+ion | 972.9  | 6H+ion | 973.3  |
|       |        | 7H+ion | 834.1  | 7H+ion | ND     |
|       |        | 8H+ion | 730.0  | 8H+ion | 722.6  |
| TPV19 |        | 4H+ion | 1458.9 | 4H+ion | ND     |
|       |        | 5H+ion | 1167.3 | 5H+ion | 1167.8 |
|       |        | 6H+ion | 972.9  | 6H+ion | 973.4  |
|       |        | 7H+ion | 834.1  | 7H+ion | 834.4  |
|       |        | 8H+ion | 730.0  | 8H+ion | 730.3  |
| TPV20 |        | 4H+ion | 1458.9 | 4H+ion | ND     |
|       |        | 5H+ion | 1167.3 | 5H+ion | 1167.9 |
|       |        | 6H+ion | 972.9  | 6H+ion | 973.1  |
|       |        | 7H+ion | 834.1  | 7H+ion | 834.2  |
|       |        | 8H+ion | 730.0  | 8H+ion | 730.2  |
| TPV21 |        | 4H+ion | 1458.9 | 4H+ion | —      |
|       |        | 5H+ion | 1167.3 | 5H+ion | 1167.8 |
|       |        | 6H+ion | 972.9  | 6H+ion | 973.3  |
|       |        | 7H+ion | 834.1  | 7H+ion | 834.4  |
|       |        | 8H+ion | 730.0  | 8H+ion | 730.3  |
| TPV22 |        | 4H+ion | 1458.9 | 4H+ion | ND     |
|       |        | 5H+ion | 1167.3 | 5H+ion | 1168.0 |

TABLE 1-4-continued

|       |        |        |        |        |
|-------|--------|--------|--------|--------|
|       | 6H+ion | 972.9  | 6H+ion | 965.4  |
|       | 7H+ion | 834.1  | 7H+ion | ND     |
|       | 8H+ion | 730.0  | 8H+ion | 719.4  |

TABLE 1-5

|       |        |        |        |        |        |
|-------|--------|--------|--------|--------|--------|
| TPV23 | 5654.4 | 4H+ion | 1414.6 | 4H+ion | ND     |
|       |        | 5H+ion | 1131.9 | 5H+ion | 1132.7 |
|       |        | 6H+ion | 943.4  | 6H+ion | 944.0  |
|       |        | 7H+ion | 808.8  | 7H+ion | 809.2  |
|       |        | 8H+ion | 707.8  | 8H+ion | 708.8  |
| TPV24 |        | 4H+ion | 1414.6 | 4H+ion | ND     |
|       |        | 5H+ion | 1131.9 | 5H+ion | 1132.5 |
|       |        | 6H+ion | 943.4  | 6H+ion | 944.8  |
|       |        | 7H+ion | 808.8  | 7H+ion | 809.4  |
|       |        | 8H+ion | 707.8  | 8H+ion | ND     |
| TPV25 |        | 4H+ion | 1414.6 | 4H+ion | ND     |
|       |        | 5H+ion | 1131.9 | 5H+ion | 1132.5 |
|       |        | 6H+ion | 943.4  | 6H+ion | 944.2  |
|       |        | 7H+ion | 808.8  | 7H+ion | 809.2  |
|       |        | 8H+ion | 707.8  | 8H+ion | 708.2  |
| TPV26 |        | 4H+ion | 1414.6 | 4H+ion | ND     |
|       |        | 5H+ion | 1131.9 | 5H+ion | 1131.6 |
|       |        | 6H+ion | 943.4  | 6H+ion | 943.5  |
|       |        | 7H+ion | 808.8  | 7H+ion | 808.6  |
|       |        | 8H+ion | 707.8  | 8H+ion | 707.7  |
| TPV27 |        | 4H+ion | 1414.6 | 4H+ion | ND     |
|       |        | 5H+ion | 1131.9 | 5H+ion | 1132.5 |
|       |        | 6H+ion | 943.4  | 6H+ion | 944.3  |
|       |        | 7H+ion | 808.8  | 7H+ion | 809.4  |
|       |        | 8H+ion | 707.8  | 8H+ion | 708.4  |
| TPV28 |        | 4H+ion | 1414.6 | 4H+ion | ND     |
|       |        | 5H+ion | 1131.9 | 5H+ion | 1133.1 |
|       |        | 6H+ion | 943.4  | 6H+ion | 939.1  |
|       |        | 7H+ion | 808.8  | 7H+ion | ND     |
|       |        | 8H+ion | 707.8  | 8H+ion | ND     |

TABLE 1-6

|       |        |        |        |        |        |
|-------|--------|--------|--------|--------|--------|
| TPV29 | 5804.6 | 4H+ion | 1452.2 | 4H+ion | ND     |
|       |        | 5H+ion | 1161.9 | 5H+ion | 1163.0 |
|       |        | 6H+ion | 968.4  | 6H+ion | 969.1  |
|       |        | 7H+ion | 830.2  | 7H+ion | 837.0  |
|       |        | 8H+ion | 726.6  | 8H+ion | ND     |
| TPV30 |        | 4H+ion | 1452.2 | 4H+ion | ND     |
|       |        | 5H+ion | 1161.9 | 5H+ion | 1164.0 |
|       |        | 6H+ion | 968.4  | 6H+ion | 968.9  |
|       |        | 7H+ion | 830.2  | 7H+ion | 825.3  |
|       |        | 8H+ion | 726.6  | 8H+ion | ND     |
| TPV31 |        | 4H+ion | 1452.2 | 4H+ion | ND     |
|       |        | 5H+ion | 1161.9 | 5H+ion | 1163.6 |
|       |        | 6H+ion | 968.4  | 6H+ion | 969.1  |
|       |        | 7H+ion | 830.2  | 7H+ion | 830.7  |
|       |        | 8H+ion | 726.6  | 8H+ion | ND     |
| TPV32 |        | 4H+ion | 1452.2 | 4H+ion | ND     |
|       |        | 5H+ion | 1161.9 | 5H+ion | 1163.0 |
|       |        | 6H+ion | 968.4  | 6H+ion | 969.2  |
|       |        | 7H+ion | 830.2  | 7H+ion | 830.5  |
|       |        | 8H+ion | 726.6  | 8H+ion | 727.0  |
| TPV33 |        | 4H+ion | 1452.2 | 4H+ion | ND     |
|       |        | 5H+ion | 1161.9 | 5H+ion | 1162.7 |
|       |        | 6H+ion | 968.4  | 6H+ion | 969.1  |
|       |        | 7H+ion | 830.2  | 7H+ion | 830.7  |
|       |        | 8H+ion | 726.6  | 8H+ion | 727.2  |
| TPV34 |        | 4H+ion | 1452.2 | 4H+ion | ND     |
|       |        | 5H+ion | 1161.9 | 5H+ion | 1171.8 |
|       |        | 6H+ion | 968.4  | 6H+ion | 969.5  |
|       |        | 7H+ion | 830.2  | 7H+ion | ND     |
|       |        | 8H+ion | 726.6  | 8H+ion | 726.8  |

TABLE 1-7

| | | | | | |
|---|---|---|---|---|---|
| TPV35 | 5658.3 | 4H+ion | 1415.6 | 4H+ion | ND |
| | | 5H+ion | 1132.7 | 5H+ion | 1133.3 |
| | | 6H+ion | 944.1 | 6H+ion | ND |
| | | 7H+ion | 809.3 | 7H+ion | 808.6 |
| | | 8H+ion | 708.3 | 8H+ion | ND |
| TPV36 | | 4H+ion | 1415.6 | 4H+ion | ND |
| | | 5H+ion | 1132.7 | 5H+ion | 1133.1 |
| | | 6H+ion | 944.1 | 6H+ion | 944.3 |
| | | 7H+ion | 809.3 | 7H+ion | 810.0 |
| | | 8H+ion | 708.3 | 8H+ion | 708.6 |
| TPV37 | 5358 | 4H+ion | 1340.5 | 4H+ion | 1340.8 |
| | | 5H+ion | 1072.6 | 5H+ion | 1072.7 |
| | | 6H+ion | 894.0 | 6H+ion | ND |
| | | 7H+ion | 766.4 | 7H+ion | 766.4 |
| | | 8H+ion | 670.8 | 8H+ion | 671.0 |
| TPV38 | | 4H+ion | 1340.5 | 4H+ion | 1340.7 |
| | | 5H+ion | 1072.6 | 5H+ion | 1072.9 |
| | | 6H+ion | 894.0 | 6H+ion | 894.1 |
| | | 7H+ion | 766.4 | 7H+ion | 766.9 |
| | | 8H+ion | 670.8 | 8H+ion | 670.7 |
| TPV39 | 5855.6 | 4H+ion | 1464.9 | 4H+ion | 1465.7 |
| | | 5H+ion | 1172.1 | 5H+ion | 1172.8 |
| | | 6H+ion | 976.9 | 6H+ion | 977.5 |
| | | 7H+ion | 837.5 | 7H+ion | 838.0 |
| | | 8H+ion | 733.0 | 8H+ion | 733.4 |
| TPV40 | 6011.8 | 4H+ion | 1504.0 | 4H+ion | 1504.7 |
| | | 5H+ion | 1203.4 | 5H+ion | 1204.0 |
| | | 6H+ion | 1003.0 | 6H+ion | 1003.5 |
| | | 7H+ion | 859.8 | 7H+ion | 860.3 |
| | | 8H+ion | 752.5 | 8H+ion | 752.8 |
| TPV41 | 5855.6 | 4H+ion | 1464.9 | 4H+ion | 1465.4 |
| | | 5H+ion | 1172.1 | 5H+ion | 1172.6 |
| | | 6H+ion | 976.9 | 6H+ion | 977.3 |
| | | 7H+ion | 837.5 | 7H+ion | 837.8 |
| | | 8H+ion | 733.0 | 8H+ion | 733.2 |

TABLE 1-8

| | | | | | |
|---|---|---|---|---|---|
| TPV42 | 5885.7 | 4H+ion | 1472.4 | 4H+ion | 1473.2 |
| | | 5H+ion | 1178.1 | 5H+ion | 1178.8 |
| | | 6H+ion | 982.0 | 6H+ion | 982.5 |
| | | 7H+ion | 841.8 | 7H+ion | 842.3 |
| | | 8H+ion | 736.7 | 8H+ion | 737.1 |
| TPV43 | 6041.9 | 4H+ion | 1511.5 | 4H+ion | ND |
| | | 5H+ion | 1209.4 | 5H+ion | 1210.0 |
| | | 6H+ion | 1008.0 | 6H+ion | 1008.6 |
| | | 7H+ion | 864.1 | 7H+ion | 864.6 |
| | | 8H+ion | 756.2 | 8H+ion | 756.6 |
| TPV44 | 6123 | 4H+ion | 1531.8 | 4H+ion | 1532.5 |
| | | 5H+ion | 1225.6 | 5H+ion | 1226.3 |
| | | 6H+ion | 1021.5 | 6H+ion | 1022.1 |
| | | 7H+ion | 875.7 | 7H+ion | 876.2 |
| | | 8H+ion | 766.4 | 8H+ion | 768.8 |
| TPV45 | 6279.2 | 4H+ion | 1570.8 | 4H+ion | 1571.5 |
| | | 5H+ion | 1256.8 | 5H+ion | 1257.5 |
| | | 6H+ion | 1047.5 | 6H+ion | 1048.1 |
| | | 7H+ion | 898.0 | 7H+ion | 898.5 |
| | | 8H+ion | 785.9 | 8H+ion | 786.3 |

"ND" indicates "not detected"

Table 2 shows the amino acid sequences of the synthesized CTL epitope peptides, and Tables 3 and 4 show the amino acid sequences of the peptides having 4 linked epitopes. The peptides having 4 linked epitopes shown in Table 4 are each prepared by, in TPV12, TPV06, and TPV26 shown in Tables 3, adding a peptide sequence consisting of arginine residues to the N terminus, and using an arginine trimer as a linker between peptides.

WT1 (SEQ ID NO: 20) was synthesized as a control peptide that binds to HLA-A2 and Her2 (SEQ ID NO: 21) was synthesized as a control peptide that binds to HLA-A24.

TABLE 2

CTL epitope peptides

| Peptide | Origin | Amino acid sequence | SEQ ID NO: |
|---|---|---|---|
| PEP1 | Lck-246 | KLVERLGAA | SEQ ID NO: 1 |
| PEP2 | WHSC2-103 | ASLDSDPWV | SEQ ID NO: 2 |
| PEP4 | SART3-302 | LLQAEAPRL | SEQ ID NO: 4 |
| PEP5 | SART2-93 | DYSARWNEI | SEQ ID NO: 5 |
| PEP6 | SART3-109 | VYDYNCHVDL | SEQ ID NO: 6 |
| PEP7 | MRP3-503 | LYAWEPSFL | SEQ ID NO: 7 |
| PEP8 | Lck-488 | DYLRSVLEDF | SEQ ID NO: 8 |
| PEP9 | SART3-734 | QIRPIFSNR | SEQ ID NO: 9 |
| PEP10 | Lck-90 | ILEQSGEWWK | SEQ ID NO: 10 |
| PEP13 | UBE2V-43 | RLQEWCSVI | SEQ ID NO: 13 |
| PEP15 | EGFR-800 | DYVREHKDNI | SEQ ID NO: 15 |
| PEP17 | MRP3-1293 | NYSVRYRPGL | SEQ ID NO: 17 |
| PEP18 | PTH-102 | RYLTQETNKV | SEQ ID NO: 18 |
| WT1 | WT1-126 | RMFPNAPYL | SEQ ID NO: 20 |
| Her2 | Her2-63 | TYLPTNASL | SEQ ID NO: 21 |

TABLE 3

Peptides having 4 linked epitopes

| Peptide | Amino acid sequence | SEQ ID NO: |
|---|---|---|
| TPV01 | PEP5-RR-PEP6-RR-PEP9-RR-PEP4 | SEQ ID NO: 22 |
| TPV02 | PEP9-RR-PEP5-RR-PEP6-RR-PEP4 | SEQ ID NO: 23 |
| TPV03 | PEP6-RR-PEP5-RR-PEP9-RR-PEP4 | SEQ ID NO: 24 |
| TPV04 | PEP6-RR-PEP9-RR-PEP5-RR-PEP4 | SEQ ID NO: 25 |
| TPV05 | PEP9-RR-PEP6-RR-PEP5-RR-PEP4 | SEQ ID NO: 26 |
| TPV06 | PEP5-RR-PEP9-RR-PEP6-RR-PEP4 | SEQ ID NO: 27 |
| TPV07 | PEP1-RR-PEP7-RR-PEP8-RR-PEP2 | SEQ ID NO: 28 |
| TPV08 | PEP1-RR-PEP8-RR-PEP7-RR-PEP2 | SEQ ID NO: 29 |
| TPV09 | PEP7-RR-PEP1-RR-PEP8-RR-PEP2 | SEQ ID NO: 30 |
| TPV10 | PEP8-RR-PEP7-RR-PEP1-RR-PEP2 | SEQ ID NO: 31 |
| TPV11 | PEP8-RR-PEP1-RR-PEP7-RR-PEP2 | SEQ ID NO: 32 |
| TPV12 | PEP7-RR-PEP13-RR-PEP8-RR-PEP2 | SEQ ID NO: 33 |
| TPV13 | PEP8-RR-PEP13-RR-PEP7-RR-PEP2 | SEQ ID NO: 34 |
| TPV14 | PEP13-RR-PEP7-RR-PEP8-RR-PEP2 | SEQ ID NO: 35 |
| TPV15 | PEP8-RR-PEP7-RR-PEP13-RR-PEP2 | SEQ ID NO: 36 |
| TPV16 | PEP13-RR-PEP8-RR-PEP7-RR-PEP2 | SEQ ID NO: 37 |
| TPV17 | PEP13-RR-PEP15-RR-PEP18-RR-PEP10 | SEQ ID NO: 38 |
| TPV18 | PEP13-RR-PEP18-RR-PEP15-RR-PEP10 | SEQ ID NO: 39 |
| TPV19 | PEP15-RR-PEP13-RR-PEP18-RR-PEP10 | SEQ ID NO: 40 |
| TPV20 | PEP15-RR-PEP18-RR-PEP13-RR-PEP10 | SEQ ID NO: 41 |
| TPV21 | PEP18-RR-PEP13-RR-PEP15-RR-PEP10 | SEQ ID NO: 42 |
| TPV22 | PEP18-RR-PEP15-RR-PEP13-RR-PEP10 | SEQ ID NO: 43 |
| TPV23 | PEP1-RR-PEP15-RR-PEP18-RR-PEP10 | SEQ ID NO: 44 |
| TPV24 | PEP1-RR-PEP18-RR-PEP15-RR-PEP10 | SEQ ID NO: 45 |
| TPV25 | PEP15-RR-PEP1-RR-PEP18-RR-PEP10 | SEQ ID NO: 46 |
| TPV26 | PEP15-RR-PEP18-RR-PEP1-RR-PEP10 | SEQ ID NO: 47 |
| TPV27 | PEP18-RR-PEP1-RR-PEP15-RR-PEP10 | SEQ ID NO: 48 |
| TPV28 | PEP18-RR-PEP15-RR-PEP1-RR-PEP10 | SEQ ID NO: 49 |
| TPV29 | PEP15-RR-PEP17-RR-PEP13-RR-PEP10 | SEQ ID NO: 50 |
| TPV30 | PEP15-RR-PEP13-RR-PEP17-RR-PEP10 | SEQ ID NO: 51 |
| TPV31 | PEP17-RR-PEP15-RR-PEP13-RR-PEP10 | SEQ ID NO: 52 |
| TPV32 | PEP17-RR-PEP13-RR-PEP15-RR-PEP10 | SEQ ID NO: 53 |
| TPV33 | PEP13-RR-PEP17-RR-PEP15-RR-PEP10 | SEQ ID NO: 54 |
| TPV34 | PEP13-RR-PEP15-RR-PEP17-RR-PEP10 | SEQ ID NO: 55 |
| TPV35 | PEP6-RR-PEP18-RR-PEP5-RR-PEP9 | SEQ ID NO: 56 |
| TPV36 | PEP6-RR-PEP5-RR-PEP18-RR-PEP9 | SEQ ID NO: 57 |

TABLE 3-continued

Peptides having 4 linked epitopes

| Peptide | Amino acid sequence | SEQ ID NO: |
|---|---|---|
| TPV37 | PEP1-RR-PEP7-RR-PEP6-RR-PEP5 | SEQ ID NO: 58 |
| TPV38 | PEP7-RR-PEP1-RR-PEP6-RR-PEP5 | SEQ ID NO: 59 |

"-RR-" represents an arginine dimer.

TABLE 4

| Peptide | Amino acid sequence | SEQ ID NO: |
|---|---|---|
| TPV39 | RRR-PEP7-RR-PEP13-RR-PEP8-RR-PEP2 | SEQ ID NO: 60 |
| TPV40 | RRRR-PEP7-RR-PEP13-RR-PEP8-RR-PEP2 | SEQ ID NO: 61 |
| TPV41 | PEP7-RRR-PEP13-RRR-PEP8-RRR-PEP2 | SEQ ID NO: 62 |
| TPV42 | RRR-PEP5-RR-PEP9-RR-PEP6-RR-PEP4 | SEQ ID NO: 63 |
| TPV43 | RRRR-PEP5-RR-PEP9-RR-PEP6-RR-PEP4 | SEQ ID NO: 64 |
| TPV44 | RRR-PEP15-RR-PEP18-RR-PEP1-RR-PEP10 | SEQ ID NO: 65 |
| TPV45 | RRRR-PEP15-RR-PEP18-RR-PEP1-RR-PEP10 | SEQ ID NO: 66 |

"-RR-" represents an arginine dimer.
"-RRR-" represents an arginine trimer.

"RRR-" and "RRRR-" are peptide sequences added to the N terminuses, which comprise 3 arginine residues and 4 arginine residues, respectively. Example 2: Inductions of epitope peptide specific CTLs in mouse model and detection of CTLs using ELISPOT The peptides having 4 linked epitopes were dissolved in distilled water (Otsuka Pharmaceutical Factory Inc.) at 2 mg/mL or 4 mg/mL, and the resulting solution was filled into the B Braun Injekt syringe. After the equivalent amount of Incomplete Freund's adjuvant (IFA) was filled into another syringe, these syringes were connected to each other using a GP syringe connector, and a solution of the peptides having 4 linked epitopes was thoroughly mixed with IFA to prepare an emulsion. The emulsion was weekly administered in amounts of 100 µL each in the vicinity of base of tail of mice (HLA-A2.1 transgenic and HLA-A24 transgenic mice (Taconic)), and administrations were carried out twice in total. Inguinal lymph nodes were corrected from mice 1 week after the final administration. A lymph node cell suspension was adjusted to $5 \times 10^6$ cells/mL using Complete Medium (RPMI-1640, 10% heat-inactivated FBS, 100 U/mL penicillin, 100 µg/mL streptomycin, and 50 µM 2-mercaptoethanol), the target CTL epitope peptide (final concentration: 10 µg/ml), recombinant mouse IL-15 (final concentration: 100 ng/mL), and recombinant mouse IL-21 (final concentration: 100 ng/mL) were added, these cells were seeded onto a 24-well plate at 1 ml/well, and were cultured in an incubator at 37° C., 5% $CO_2$ for 8 days. Thereafter, the cells were collected and seeded on an anti-IFN-γ antibody-immobilized plate included in the Murine IFN-γ ELISpot Kit (GEN-PROBE) at $1 \times 10^5$ cells/well. Subsequently, splenocytes obtained from the spleen of syngeneic mouse and irradiated with 30-Gy X-rays were plated on the same plate at $1 \times 10^5$ cells/well as antigen presenting cells, the target CTL epitope peptide or the negative control peptide (final concentration: 10 µg/mL) were added, and incubated in an incubator at 37° C., 5% $CO_2$ overnight. On the following day, spots which indicate existence of IFN-γ-producing cells were colored according to manufacturer's instructions. The number of IFN-γ-producing cell spots was quantified using an ELISPOT analyzer (Immunospot S6, Cellular Technology Ltd.). Induction of CTL epitope peptide specific CTL was evaluated as positive when the number of IFN-γ-producing cell spots in the wells supplemented with the target CTL epitope peptides was significantly higher than that observed in the wells supplemented with the negative control peptides (Student's t-test, p<0.05). WT1 or Her2 was used as the negative control peptide. In order to visualize the CTL induction level, the results of the following equation were designated as "A" (the average number of IFN-γ-producing cell spots in wells supplemented with the target CTL epitope peptides)–(the average number of IFN-γ-producing cell spots in wells supplemented with the negative control peptides). The results are represented as positive in case of 10≤Δ<100; medium positive in case of 100≤Δ<200; and strongly positive in case of 200≤Δ.

FIGS. 3-1 to 3-4 show the results of evaluation of CTL epitope peptide specific CTL induction. When the peptide having 4 linked epitopes according to the present invention has one or more features selected from among the features <1> to <3> below, as shown in FIGS. 3-1 to 3-4, at least 3 types of CTLs of the 4 types of linked CTL epitope peptides were induced.

<1> The peptide comprises PEP4 at the C terminus.

<2> The peptide comprises PEP6 and PEP5 at the C terminus successively disposed in such order from the N terminus via a linker.

<3> The peptide comprises PEP5, PEP6, PEP5, and PEP18.

When a peptide sequence consisting of arginine residues was further added to the N terminus or when a peptide-peptide linker was an arginine trimer, as shown in FIG. 3-4, CTL was satisfactorily induced as described above.

In the case of peptides having 4 linked epitopes having the linking order shown in CPV01 to CPV16, however, CTL induction was not observed in three or more peptides, as shown in FIGS. 3-1 to 3-3.

Specifically, even if the peptides having 4 linked CTL epitopes were composed of 4 types of epitope peptides selected from particular 13 types of epitope peptides (PEP1, PEP2, PEP4, PEP5, PEP6, PEP7, PEP5, PEP5, PEP10, PEP13, PEP15, PEP17, and PEP18) (i.e., CPV14, CPV15, and CPV16), CTL induction was not observed in three or more peptides in the peptides having 4 linked CTL epitopes.

Example 3: Prediction of Peptide Cleavage Position with Human 20S Immunoproteasomes (i20S)

Cleavage samples of peptides having 4 linked epitopes were prepared in the manner described below. Specifically, peptides having 4 linked epitopes were diluted to 66.7 µg/mL with a reaction buffer (20 mM HEPES-KOH, pH 7.8, 2 mM $MgAc_2$, 2 mM dithiothreitol), and the resultant was dispensed into reaction tubes in amounts of 300 µL per tube. Human 20S immunoproteasomes (R&D systems) were added thereto in amounts of 2 µg per tube, the mixtures were agitated, and the resultants were then subjected to incubation with shaking at 37° C. for 1, 2, or 4 hours. Thereafter, acetic acid was added in amounts of 30 µL per tube, so as to terminate the enzymatic reactions, and the samples were lyophilized in a freezer at −80° C. immediately.

Subsequently, the obtained cleavage samples of the peptides having 4 linked epitopes were applied to the LC/MS-MS systems (Acquity UPLC system, Waters; Synapt G2 HDMS, Waters), so as to perform comprehensive analysis of the molecular weights of the peptide fragments. With the use of analytical software (MassLynx, ver. 4.1, SCN712, Waters), the samples were analyzed, and the peptide fragments were identified. The peptides having 4 linked epitopes were evaluated to be cleavable upon development of any of a peptide in which the epitope peptide was cleaved, a peptide comprising arginine residues added to the N terminus of the epitope peptide, or a peptide comprising an arginine dimer added to the N terminus of the epitope peptide, as a result of cleavage with immunoproteasomes.

The results of analysis conducted with the use of the immunoproteasomes shown in FIGS. 3-1 to 3-4 demonstrate that two types of CTL epitope peptides, PEP2 and PEP10, are required to be located at positions nearest to the C terminus of the peptide having 4 linked epitopes, so as to determine the C terminal amino acids of the CTL epitope peptides of interest. Accordingly, it is preferable that PEP2 or PEP10 be linked to the C terminus of the peptide having 4 linked epitopes according to the present invention.

Example 4: Preparation of CTL Epitope Peptide-Immobilized Beads

Peptides were immobilized onto xMAP Multi-Analyte COOH Microspheres (Luminex Corporation; hereafter referred to as "beads") in the manner described below. The beads were washed with MES buffer (0.1 M MES-NaOH; pH 7.0), and the supernatant was then removed by centrifugation. This washing process was repeated twice and the beads were then suspended in 75 µL of an MES buffer. A CTL epitope peptide solution (100 µL, 1 mg/mL) and 5 µL of 10 mg/mL EDC (1-ethyl-3-(3-dimethylaminopropyl)carbodiimide hydrochloride) were added to the bead suspension, followed by thorough mixing. Thereafter, the reaction was performed at 30° C. in the dark overnight. After the removal of the supernatant by centrifugation on the following day, 125 µL of 1 M Tris-HCl was added, and incubation was carried out at 30° C. in the dark for 30 minutes. After the supernatant was removed again, the beads were washed twice with a wash buffer (PBS(−), 0.05% Tween 20) and were suspended in Immunoblock (DS Pharma Biomedical Co., Ltd.). Thus, immobilization of the CTL epitope peptide was completed.

Example 5: Measurement of CTL-Epitope Specific IgG Antibody Titer

The peptides having 4 linked epitopes according to the present invention were dissolved in distilled water (Otsuka Pharmaceutical Factory Inc.) at 2 mg/mL, and the resulting solution was filled into a B Braun Injekt syringe. After the equivalent amount of IFA was filled into another syringe, these syringes were connected to each other using a GP syringe connector, and a solution of the peptides having 4 linked epitopes was thoroughly mixed with IFA to prepare an emulsion. The emulsion was weekly administered in amounts of 100 µL each in the vicinity of the base of the tail of CBF1 mice (C57BL/6×Balb/c F1), and administration was carried out three times in total. The blood was collected from mice 1 week after the final administration to obtain serum samples. As control samples, emulsions were prepared using mixtures of 4 types of peptides selected from among PEP1, PEP2, PEP4, PEP5, PEP6, PEP7, PEP8, PEP9, PEP10, PEP13, PEP15, and PEP18 (1 mg/mL each), and the resulting emulsions were administered in accordance with the same schedule as with the peptide having 4 linked epitopes (the mixture-administered group).

The CTL epitope peptide-immobilized beads diluted with Immunoblock were dispensed into wells of a 96-well filter plate. The dispensed beads were washed with a wash buffer, and, subsequently, 100 µL of mouse serum samples diluted 200-fold with Immunoblock were added into each wells. The plate was incubated for 90 minutes at 30° C. with 600 rpm mixing. After the three times of plate washing with a wash buffer, 100 µL of biotinylated-anti-mouse IgG (H+L) (Vector Laboratories) diluted 500-fold with Immunoblock was added into each well, and the plate was incubated for 60 minutes at 30° C. with 600 rpm mixing After the three times of plate washing with a wash buffer, 100 µL of streptavidin-R-phycoerythrin conjugate (Invitrogen) diluted 500-fold with Immunoblock was added into each well, and the plate was incubated for 30 minutes at 30° C. with 600 rpm mixing. After the three times of plate washing with a wash buffer, 100 µL of a wash buffer was added into each well to suspend beads, and the mean fluorescence intensity of PE which specifically bound to relevant beads was measured using the Bio-Plex Suspension Array System (BIO-RAD).

The results of measurement of the CTL-epitope specific IgG antibody titer are as shown in FIGS. 4-1 to 4-3. FIGS. 4-1 to 4-3 show the degree of the CTL epitope specific IgG antibody production compared with that of the negative control group (hereafter abbreviated as the "IFA group") mice. The results obtained from the IFA group to which an emulsion prepared by mixing equivalent amounts of IFA and distilled water (Otsuka Pharmaceutical Factory Inc.) had been administrated were compared with the results obtained in accordance with the same treatment schedule as that of the CTL epitope peptide mixture or the peptide having 4 linked epitopes.

As shown in FIGS. 4-1 to 4-3, the induction of the CTL epitope specific IgG antibody production was weak and frequency thereof was low in the mixture-administered group. When the peptide having 4 linked epitopes was administered, in contrast, strong induction of CTL epitope specific IgG antibody production was observed frequently. In addition, the amount of IgG production was found to be significantly higher (e.g., several ten times to several hundred times higher than that observed in the IFA group) depending on the type of the peptide having 4 linked epitopes administered.

These results demonstrate that administration of the peptide having 4 linked epitopes can more strongly activate antitumor immunity than administration of a mixture of CTL epitope peptides constituting the peptide having 4 linked epitopes.

For a cancer patient who has been treated with a peptide vaccine for cancer, induction of CTL epitope peptide specific IgG production and induction of epitope peptide specific CTL are both effective for life prolongation. Accordingly, the life prolongation effects attained by the present invention are superior to those attained by cancer treatment using peptide vaccines comprising known CTL epitope peptides or mixtures thereof. Therefore, the peptide having 4 linked epitopes according to the present invention can be suitably used as a therapeutic and/or preventive agent for cancers or diseases caused thereby and peptide vaccines for cancer that can provide superior treatment outcomes compared with cancer treatment using peptide vaccines comprising known CTL epitope peptides or mixtures thereof.

All publications, patents, and patent applications cited herein are incorporated herein by reference in their entirety.

The invention claimed is:

1. A peptide having the general formula: A-(L)-B-(L)-C-(L)-D
wherein (L) is a linker and wherein A, B, C, and D consist of a total of four CTL epitope peptides and are independently selected from the group consisting of:
  PEP1 as represented by SEQ ID NO: 1;
  PEP2 as represented by SEQ ID NO: 2;
  PEP4 as represented by SEQ ID NO: 4;
  PEP5 as represented by SEQ ID NO: 5;
  PEP6 as represented by SEQ ID NO: 6;
  PEP7 as represented by SEQ ID NO: 7;
  PEP8 as represented by SEQ ID NO: 8;
  PEP9 as represented by SEQ ID NO: 9;
  PEP10 as represented by SEQ ID NO: 10;
  PEP13 as represented by SEQ ID NO: 13;
  PEP15 as represented by SEQ ID NO; 15;
  PEP17 as represented by SEQ ID NO: 17; and
  PEP18 as represented by SEQ II) NO: 18; and wherein
  (a) the peptide comprises PEP2 at the C terminus but not when the peptide comprises PEP7 at the N terminus followed by PEP8; or
  (b) the peptide comprises PEP4 at the C terminus; or
  (c) the peptide comprises PEP10 at the C terminus; or
  (d) the peptide comprises PEP5 at the C terminus preceded by PEP6; or (e) the peptide-consists of PEP5, PEP6, PEP9, and PEP18, and
wherein the peptide optionally comprises hydrophilic amino acids at the N terminus or C terminus to improve solubility of the peptide.

2. The peptide according to claim 1, wherein the CTL epitope peptides are 4 non-redundant peptides selected from the group consisting of PEP1, PEP2, PEP4, PEP5, PEP6, PEP7, PEP8, PEP9, PEP10, PEP13, PEP15, PE17, and PEP18.

3. The peptide according to claim 1 selected from the group consisting of:
(i) the peptide comprising PEP2 at the C terminus and also 3 CTL epitope peptides selected from the group consisting of PEP1, PEP7, PEP5, and PEP13 but not when the peptide comprises PEP7 at the N terminus followed by PEP8;
(ii) the peptide consisting of PEP4 at the C terminus and also PEP5, PEP6, and PEP9;
(iii) the peptide consisting of PEP10 at the C terminus and also 3 CTL epitope peptides selected from the group consisting of PEP1, PEP13, PEP15, PEP17, and PEP18;
(iv) the peptide consisting of PEP5 at the C terminus preceded by PEP6, also PEP1 and PEP7; and
(v) the peptide consisting of PEP9 at the C terminus and also PEP5, PEP6, and PEP18.

4. The peptide according to claim 1, wherein the ordered arrangement of the peptide from the N terminus is selected from the group consisting of:
PEP5-(L)-PEP6-(L)-PEP5-(L)-PEP4;
PEP9-(L)-PEP5-(L)-PEP6-(L)-PEP4;
PEP6-(L)-PEP5-(L)-PEP9-(L)-PEP4;
PEP6-(L)-PEP9-(L)-PEP5-(L)-PEP4;
PEP9-(L)-PEP6-(L)-PEP5-(L)-PEP4;
PEP5-(L)-PEP9-(L)-PEP6-(L)-PEP4;
PEP1-(L)-PEP7-(L)-PEP8-(L)-PEP2;
PEP1-(L)-PEP8-(L)-PEP7-(L)-PEP2;
PEP7-(L)-PEP1-(L)-PEP8-(L)-PEP2;
PEP8-(L)-PEP7-(L)-PEP1-(L)-PEP2;
PEP8-(L)-PEP1-(L)-PEP7-(L)-PEP2;
PEP7-(L)-PEP13-(L)-PEP8-(L)-PEP2;
PEP8-(L)-PEP13-(L)-PEP7-(L)-PEP2;
PEP13-(L)-PEP7-(L)-PEP8-(L)-PEP2;
PEP8-(L)-PEP7-(L)-PEP13-(L)-PEP2;
PEP13-(L)-PEP8-(L)-PEP7-(L)-PEP2;
PEP13-(L)-PEP15-(L)-PEP18-(L)-PEP10;
PEP13-(L)-PEP18-(L)-PEP15-(L)-PEP10;
PEP15-(L)-PEP13-(L)-PEP18-(L)-PEP10;
PEP15-(L)-PEP18-(L)-PEP13-(L)-PEP10;
PEP18-(L)-PEP13-(L)-PEP15-(L)-PEP10;
PEP18-(L)-PEP15-(L)-PEP13-(L)-PEP10;
PEP1-(L)-PEP15-(L)-PEP18-(L)-PEP10;
PEP1-(L)-PEP18-(L)-PEP15-(L)-PEP10;
PEP15-(L)-PEP1-(L)-PEP18-(L)-PEP10;
PEP15-(L)-PEP18-(L)-PEP1-(L)-PEP10;
PEP18-(L)-PEP1-(L)-PEP15-(L)-PEP10;
PEP18-(L)-PEP15-(L)-PEP1-(L)-PEP10;
PEP15-(L)-PEP17-(L)-PEP13-(L)-PEP10;
PEP15-(L)-PEP13-(L)-PEP17-(L)-PEP10;
PEP17-(L)-PEP15-(L)-PEP13-(L)-PEP10;
PEP17-(L)-PEP13-(L)-PEP15-(L)-PEP10;
PEP13-(L)-PEP17-(L)-PEP15-(L)-PEP10;
PEP13-(L)-PEP15-(L)-PEP17-(L)-PEP10;
PEP6-(L)-PEP18-(L)-PEP5-(L)-PEP9;
PEP6-(L)-PEP5-(L)-PEP18-(L)-PEP9;
PEP1-(L)-PEP7-(L)-PEP6-(L)-PEP5; or
PEP7-(L)-PEP1-(L)-PEP6-(L)-PEP5.

5. The peptide according to claim 1, wherein the linker is an amino acid linker.

6. The peptide according to claim 5, wherein the amino acid linker is an arginine dimer or an arginine trimer.

7. The peptide according to claim 1, wherein the hydrophilic amino acids are located at the N terminus.

8. The peptide according to claim 1, wherein the hydrophilic amino acids comprise an arginine trimer or an arginine tetramer.

9. The peptide according to claim 1, which consists of the amino acid sequence as shown in SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, or SEQ ID NO: 66.

10. A method for stimulating a CTL comprising contacting peripheral blood lymphocytes with the peptide according to any one of claims 1 to 9.

11. A pharmaceutical composition comprising, as an active ingredient, the peptide according to claim 1.

12. A pharmaceutical composition comprising two or more distinct peptides according to claim 1.

13. A method for treating cancer comprising administering to a cancer patient the peptide according to any one of claims 1 to 9, or the pharmaceutical composition according to any one of claims 11 to 12.

* * * * *

UNITED STATES PATENT AND TRADEMARK OFFICE
CERTIFICATE OF CORRECTION

PATENT NO.        : 10,137,183 B2
APPLICATION NO.   : 15/030678
DATED             : November 27, 2018
INVENTOR(S)       : Satoshi Fukaya et al.

It is certified that error appears in the above-identified patent and that said Letters Patent is hereby corrected as shown below:

In the Claims

Column 53, Claim 3, Line 15:
PEP1, PEP7, PEP5 and PEP13
Should read:
-- PEP1, PEP7, PEP8 and PEP13 --.

Column 53, Claim 4, Line 31:
PEP5-(L)-PEP6-(L)-PEP5-(L)-PEP4;
Should read:
-- PEP5-(L)-PEP6-(L)-PEP9-(L)-PEP4; --.

Signed and Sealed this
Thirtieth Day of July, 2019

Andrei Iancu
*Director of the United States Patent and Trademark Office*

SEQUENCE LISTING

<160> NUMBER OF SEQ ID NOS: 66

<210> SEQ ID NO 1
<211> LENGTH: 9
<212> TYPE: PRT
<213> ORGANISM: Homo sapiens

<400> SEQUENCE: 1

Lys Leu Val Glu Arg Leu Gly Ala Ala
1               5

<210> SEQ ID NO 2
<211> LENGTH: 9
<212> TYPE: PRT
<213> ORGANISM: Homo sapiens

<400> SEQUENCE: 2

Ala Ser Leu Asp Ser Asp Pro Trp Val
1               5

<210> SEQ ID NO 3
<211> LENGTH: 9
<212> TYPE: PRT
<213> ORGANISM: Homo sapiens

<400> SEQUENCE: 3

Ala Leu Val Glu Phe Glu Asp Val Leu
1               5

<210> SEQ ID NO 4
<211> LENGTH: 9
<212> TYPE: PRT
<213> ORGANISM: Homo sapiens

<400> SEQUENCE: 4

Leu Leu Gln Ala Glu Ala Pro Arg Leu
1               5

<210> SEQ ID NO 5
<211> LENGTH: 9
<212> TYPE: PRT
<213> ORGANISM: Homo sapiens

<400> SEQUENCE: 5

Asp Tyr Ser Ala Arg Trp Asn Glu Ile
1               5

<210> SEQ ID NO 6
<211> LENGTH: 10
<212> TYPE: PRT
<213> ORGANISM: Homo sapiens

<400> SEQUENCE: 6

Val Tyr Asp Tyr Asn Cys His Val Asp Leu
1               5                   10

<210> SEQ ID NO 7
<211> LENGTH: 9
<212> TYPE: PRT
<213> ORGANISM: Homo sapiens

<400> SEQUENCE: 7

Leu Tyr Ala Trp Glu Pro Ser Phe Leu
1               5

```
<210> SEQ ID NO 8
<211> LENGTH: 10
<212> TYPE: PRT
<213> ORGANISM: Homo sapiens

<400> SEQUENCE: 8

Asp Tyr Leu Arg Ser Val Leu Glu Asp Phe
1               5                   10

<210> SEQ ID NO 9
<211> LENGTH: 9
<212> TYPE: PRT
<213> ORGANISM: Homo sapiens

<400> SEQUENCE: 9

Gln Ile Arg Pro Ile Phe Ser Asn Arg
1               5

<210> SEQ ID NO 10
<211> LENGTH: 10
<212> TYPE: PRT
<213> ORGANISM: Homo sapiens

<400> SEQUENCE: 10

Ile Leu Glu Gln Ser Gly Glu Trp Trp Lys
1               5                   10

<210> SEQ ID NO 11
<211> LENGTH: 10
<212> TYPE: PRT
<213> ORGANISM: Homo sapiens

<400> SEQUENCE: 11

Val Ile Gln Asn Leu Glu Arg Gly Tyr Arg
1               5                   10

<210> SEQ ID NO 12
<211> LENGTH: 10
<212> TYPE: PRT
<213> ORGANISM: Homo sapiens

<400> SEQUENCE: 12

Lys Leu Lys His Tyr Gly Pro Gly Trp Val
1               5                   10

<210> SEQ ID NO 13
<211> LENGTH: 9
<212> TYPE: PRT
<213> ORGANISM: Homo sapiens

<400> SEQUENCE: 13

Arg Leu Gln Glu Trp Cys Ser Val Ile
1               5

<210> SEQ ID NO 14
<211> LENGTH: 9
<212> TYPE: PRT
<213> ORGANISM: Homo sapiens

<400> SEQUENCE: 14

Ile Leu Gly Glu Leu Arg Glu Lys Val
1               5

<210> SEQ ID NO 15
```

```
<211> LENGTH: 10
<212> TYPE: PRT
<213> ORGANISM: Homo sapiens

<400> SEQUENCE: 15

Asp Tyr Val Arg Glu His Lys Asp Asn Ile
1               5                   10

<210> SEQ ID NO 16
<211> LENGTH: 9
<212> TYPE: PRT
<213> ORGANISM: Homo sapiens

<400> SEQUENCE: 16

His Tyr Thr Asn Ala Ser Asp Gly Leu
1               5

<210> SEQ ID NO 17
<211> LENGTH: 10
<212> TYPE: PRT
<213> ORGANISM: Homo sapiens

<400> SEQUENCE: 17

Asn Tyr Ser Val Arg Tyr Arg Pro Gly Leu
1               5                   10

<210> SEQ ID NO 18
<211> LENGTH: 10
<212> TYPE: PRT
<213> ORGANISM: Homo sapiens

<400> SEQUENCE: 18

Arg Tyr Leu Thr Gln Glu Thr Asn Lys Val
1               5                   10

<210> SEQ ID NO 19
<211> LENGTH: 9
<212> TYPE: PRT
<213> ORGANISM: Homo sapiens

<400> SEQUENCE: 19

Thr Phe Asp Tyr Leu Arg Ser Val Leu
1               5

<210> SEQ ID NO 20
<211> LENGTH: 9
<212> TYPE: PRT
<213> ORGANISM: Homo sapiens

<400> SEQUENCE: 20

Arg Met Phe Pro Asn Ala Pro Tyr Leu
1               5

<210> SEQ ID NO 21
<211> LENGTH: 9
<212> TYPE: PRT
<213> ORGANISM: Homo sapiens

<400> SEQUENCE: 21

Thr Tyr Leu Pro Thr Asn Ala Ser Leu
1               5

<210> SEQ ID NO 22
<211> LENGTH: 43
<212> TYPE: PRT
```

<213> ORGANISM: Artificial
<220> FEATURE:
<223> OTHER INFORMATION: synthetic peptide

<400> SEQUENCE: 22

Asp Tyr Ser Ala Arg Trp Asn Glu Ile Arg Arg Val Tyr Asp Tyr Asn
1               5                   10                  15

Cys His Val Asp Leu Arg Arg Gln Ile Arg Pro Ile Phe Ser Asn Arg
            20                  25                  30

Arg Arg Leu Leu Gln Ala Glu Ala Pro Arg Leu
        35                  40

<210> SEQ ID NO 23
<211> LENGTH: 43
<212> TYPE: PRT
<213> ORGANISM: Artificial
<220> FEATURE:
<223> OTHER INFORMATION: synthetic peptide

<400> SEQUENCE: 23

Gln Ile Arg Pro Ile Phe Ser Asn Arg Arg Arg Asp Tyr Ser Ala Arg
1               5                   10                  15

Trp Asn Glu Ile Arg Arg Val Tyr Asp Tyr Asn Cys His Val Asp Leu
            20                  25                  30

Arg Arg Leu Leu Gln Ala Glu Ala Pro Arg Leu
        35                  40

<210> SEQ ID NO 24
<211> LENGTH: 43
<212> TYPE: PRT
<213> ORGANISM: Artificial
<220> FEATURE:
<223> OTHER INFORMATION: synthetic peptide

<400> SEQUENCE: 24

Val Tyr Asp Tyr Asn Cys His Val Asp Leu Arg Asp Tyr Ser Ala
1               5                   10                  15

Arg Trp Asn Glu Ile Arg Arg Gln Ile Arg Pro Ile Phe Ser Asn Arg
            20                  25                  30

Arg Arg Leu Leu Gln Ala Glu Ala Pro Arg Leu
        35                  40

<210> SEQ ID NO 25
<211> LENGTH: 43
<212> TYPE: PRT
<213> ORGANISM: Artificial
<220> FEATURE:
<223> OTHER INFORMATION: synthetic peptide

<400> SEQUENCE: 25

Val Tyr Asp Tyr Asn Cys His Val Asp Leu Arg Arg Gln Ile Arg Pro
1               5                   10                  15

Ile Phe Ser Asn Arg Arg Arg Asp Tyr Ser Ala Arg Trp Asn Glu Ile
            20                  25                  30

Arg Arg Leu Leu Gln Ala Glu Ala Pro Arg Leu
        35                  40

<210> SEQ ID NO 26
<211> LENGTH: 43
<212> TYPE: PRT
<213> ORGANISM: Artificial
<220> FEATURE:
<223> OTHER INFORMATION: synthetic peptide

<400> SEQUENCE: 26

Gln Ile Arg Pro Ile Phe Ser Asn Arg Arg Val Tyr Asp Tyr Asn
1               5                   10                  15

Cys His Val Asp Leu Arg Arg Asp Tyr Ser Ala Arg Trp Asn Glu Ile
            20                  25                  30

Arg Arg Leu Leu Gln Ala Glu Ala Pro Arg Leu
        35                  40

<210> SEQ ID NO 27
<211> LENGTH: 43
<212> TYPE: PRT
<213> ORGANISM: Artificial
<220> FEATURE:
<223> OTHER INFORMATION: synthetic peptide

<400> SEQUENCE: 27

Asp Tyr Ser Ala Arg Trp Asn Glu Ile Arg Arg Gln Ile Arg Pro Ile
1               5                   10                  15

Phe Ser Asn Arg Arg Val Tyr Asp Tyr Asn Cys His Val Asp Leu
            20                  25                  30

Arg Arg Leu Leu Gln Ala Glu Ala Pro Arg Leu
        35                  40

<210> SEQ ID NO 28
<211> LENGTH: 43
<212> TYPE: PRT
<213> ORGANISM: Artificial
<220> FEATURE:
<223> OTHER INFORMATION: synthetic peptide

<400> SEQUENCE: 28

Lys Leu Val Glu Arg Leu Gly Ala Ala Arg Arg Leu Tyr Ala Trp Glu
1               5                   10                  15

Pro Ser Phe Leu Arg Arg Asp Tyr Leu Arg Ser Val Leu Glu Asp Phe
            20                  25                  30

Arg Arg Ala Ser Leu Asp Ser Asp Pro Trp Val
        35                  40

<210> SEQ ID NO 29
<211> LENGTH: 43
<212> TYPE: PRT
<213> ORGANISM: Artificial
<220> FEATURE:
<223> OTHER INFORMATION: synthetic peptide

<400> SEQUENCE: 29

Lys Leu Val Glu Arg Leu Gly Ala Ala Arg Arg Asp Tyr Leu Arg Ser
1               5                   10                  15

Val Leu Glu Asp Phe Arg Arg Leu Tyr Ala Trp Glu Pro Ser Phe Leu
            20                  25                  30

Arg Arg Ala Ser Leu Asp Ser Asp Pro Trp Val
        35                  40

<210> SEQ ID NO 30
<211> LENGTH: 43
<212> TYPE: PRT
<213> ORGANISM: Artificial
<220> FEATURE:
<223> OTHER INFORMATION: synthetic peptide

<400> SEQUENCE: 30

Leu Tyr Ala Trp Glu Pro Ser Phe Leu Arg Arg Lys Leu Val Glu Arg
1               5                   10                  15

Leu Gly Ala Ala Arg Arg Asp Tyr Leu Arg Ser Val Leu Glu Asp Phe
            20                  25                  30

Arg Arg Ala Ser Leu Asp Ser Asp Pro Trp Val
        35                  40

<210> SEQ ID NO 31
<211> LENGTH: 43
<212> TYPE: PRT
<213> ORGANISM: Artificial
<220> FEATURE:
<223> OTHER INFORMATION: synthetic peptide

<400> SEQUENCE: 31

Asp Tyr Leu Arg Ser Val Leu Glu Asp Phe Arg Arg Leu Tyr Ala Trp
1               5                   10                  15

Glu Pro Ser Phe Leu Arg Arg Lys Leu Val Glu Arg Leu Gly Ala Ala
            20                  25                  30

Arg Arg Ala Ser Leu Asp Ser Asp Pro Trp Val
        35                  40

<210> SEQ ID NO 32
<211> LENGTH: 43
<212> TYPE: PRT
<213> ORGANISM: Artificial
<220> FEATURE:
<223> OTHER INFORMATION: synthetic peptide

<400> SEQUENCE: 32

Asp Tyr Leu Arg Ser Val Leu Glu Asp Phe Arg Arg Lys Leu Val Glu
1               5                   10                  15

Arg Leu Gly Ala Ala Arg Arg Leu Tyr Ala Trp Glu Pro Ser Phe Leu
            20                  25                  30

Arg Arg Ala Ser Leu Asp Ser Asp Pro Trp Val
        35                  40

<210> SEQ ID NO 33
<211> LENGTH: 43
<212> TYPE: PRT
<213> ORGANISM: Artificial
<220> FEATURE:
<223> OTHER INFORMATION: synthetic peptide

<400> SEQUENCE: 33

Leu Tyr Ala Trp Glu Pro Ser Phe Leu Arg Arg Leu Gln Glu Trp
1               5                   10                  15

Cys Ser Val Ile Arg Arg Asp Tyr Leu Arg Ser Val Leu Glu Asp Phe
            20                  25                  30

Arg Arg Ala Ser Leu Asp Ser Asp Pro Trp Val
        35                  40

<210> SEQ ID NO 34
<211> LENGTH: 43
<212> TYPE: PRT
<213> ORGANISM: Artificial
<220> FEATURE:
<223> OTHER INFORMATION: synthetic peptide

<400> SEQUENCE: 34

Asp Tyr Leu Arg Ser Val Leu Glu Asp Phe Arg Arg Leu Gln Glu
1               5                   10                  15

```
Trp Cys Ser Val Ile Arg Arg Leu Tyr Ala Trp Glu Pro Ser Phe Leu
            20                  25                  30

Arg Arg Ala Ser Leu Asp Ser Asp Pro Trp Val
        35                  40
```

<210> SEQ ID NO 35
<211> LENGTH: 43
<212> TYPE: PRT
<213> ORGANISM: Artificial
<220> FEATURE:
<223> OTHER INFORMATION: synthetic peptide

<400> SEQUENCE: 35

```
Arg Leu Gln Glu Trp Cys Ser Val Ile Arg Arg Leu Tyr Ala Trp Glu
1               5                   10                  15

Pro Ser Phe Leu Arg Arg Asp Tyr Leu Arg Ser Val Leu Glu Asp Phe
            20                  25                  30

Arg Arg Ala Ser Leu Asp Ser Asp Pro Trp Val
        35                  40
```

<210> SEQ ID NO 36
<211> LENGTH: 43
<212> TYPE: PRT
<213> ORGANISM: Artificial
<220> FEATURE:
<223> OTHER INFORMATION: synthetic peptide

<400> SEQUENCE: 36

```
Asp Tyr Leu Arg Ser Val Leu Glu Asp Phe Arg Arg Leu Tyr Ala Trp
1               5                   10                  15

Glu Pro Ser Phe Leu Arg Arg Arg Leu Gln Glu Trp Cys Ser Val Ile
            20                  25                  30

Arg Arg Ala Ser Leu Asp Ser Asp Pro Trp Val
        35                  40
```

<210> SEQ ID NO 37
<211> LENGTH: 43
<212> TYPE: PRT
<213> ORGANISM: Artificial
<220> FEATURE:
<223> OTHER INFORMATION: synthetic peptide

<400> SEQUENCE: 37

```
Arg Leu Gln Glu Trp Cys Ser Val Ile Arg Arg Asp Tyr Leu Arg Ser
1               5                   10                  15

Val Leu Glu Asp Phe Arg Arg Leu Tyr Ala Trp Glu Pro Ser Phe Leu
            20                  25                  30

Arg Arg Ala Ser Leu Asp Ser Asp Pro Trp Val
        35                  40
```

<210> SEQ ID NO 38
<211> LENGTH: 45
<212> TYPE: PRT
<213> ORGANISM: Artificial
<220> FEATURE:
<223> OTHER INFORMATION: synthetic peptide

<400> SEQUENCE: 38

```
Arg Leu Gln Glu Trp Cys Ser Val Ile Arg Arg Asp Tyr Val Arg Glu
1               5                   10                  15

His Lys Asp Asn Ile Arg Arg Tyr Leu Thr Gln Glu Thr Asn Lys
            20                  25                  30
```

Val Arg Arg Ile Leu Glu Gln Ser Gly Glu Trp Trp Lys
        35                  40                  45

<210> SEQ ID NO 39
<211> LENGTH: 45
<212> TYPE: PRT
<213> ORGANISM: Artificial
<220> FEATURE:
<223> OTHER INFORMATION: synthetic peptide

<400> SEQUENCE: 39

Arg Leu Gln Glu Trp Cys Ser Val Ile Arg Arg Tyr Leu Thr Gln
1               5                   10                  15

Glu Thr Asn Lys Val Arg Arg Asp Tyr Val Arg Glu His Lys Asp Asn
                20                  25                  30

Ile Arg Arg Ile Leu Glu Gln Ser Gly Glu Trp Trp Lys
        35                  40                  45

<210> SEQ ID NO 40
<211> LENGTH: 45
<212> TYPE: PRT
<213> ORGANISM: Artificial
<220> FEATURE:
<223> OTHER INFORMATION: synthetic peptide

<400> SEQUENCE: 40

Asp Tyr Val Arg Glu His Lys Asp Asn Ile Arg Arg Leu Gln Glu
1               5                   10                  15

Trp Cys Ser Val Ile Arg Arg Arg Tyr Leu Thr Gln Glu Thr Asn Lys
                20                  25                  30

Val Arg Arg Ile Leu Glu Gln Ser Gly Glu Trp Trp Lys
        35                  40                  45

<210> SEQ ID NO 41
<211> LENGTH: 45
<212> TYPE: PRT
<213> ORGANISM: Artificial
<220> FEATURE:
<223> OTHER INFORMATION: synthetic peptide

<400> SEQUENCE: 41

Asp Tyr Val Arg Glu His Lys Asp Asn Ile Arg Arg Tyr Leu Thr
1               5                   10                  15

Gln Glu Thr Asn Lys Val Arg Arg Leu Gln Glu Trp Cys Ser Val
                20                  25                  30

Ile Arg Arg Ile Leu Glu Gln Ser Gly Glu Trp Trp Lys
        35                  40                  45

<210> SEQ ID NO 42
<211> LENGTH: 45
<212> TYPE: PRT
<213> ORGANISM: Artificial
<220> FEATURE:
<223> OTHER INFORMATION: synthetic peptide

<400> SEQUENCE: 42

Arg Tyr Leu Thr Gln Glu Thr Asn Lys Val Arg Arg Leu Gln Glu
1               5                   10                  15

Trp Cys Ser Val Ile Arg Arg Asp Tyr Val Arg Glu His Lys Asp Asn
                20                  25                  30

Ile Arg Arg Ile Leu Glu Gln Ser Gly Glu Trp Trp Lys
        35                  40                  45

<210> SEQ ID NO 43
<211> LENGTH: 45
<212> TYPE: PRT
<213> ORGANISM: Artificial
<220> FEATURE:
<223> OTHER INFORMATION: synthetic peptide

<400> SEQUENCE: 43

```
Arg Tyr Leu Thr Gln Glu Thr Asn Lys Val Arg Arg Asp Tyr Val Arg
1               5                   10                  15

Glu His Lys Asp Asn Ile Arg Arg Arg Leu Gln Glu Trp Cys Ser Val
                20                  25                  30

Ile Arg Arg Ile Leu Glu Gln Ser Gly Glu Trp Trp Lys
            35                  40                  45
```

<210> SEQ ID NO 44
<211> LENGTH: 45
<212> TYPE: PRT
<213> ORGANISM: Artificial
<220> FEATURE:
<223> OTHER INFORMATION: synthetic peptide

<400> SEQUENCE: 44

```
Lys Leu Val Glu Arg Leu Gly Ala Ala Arg Arg Asp Tyr Val Arg Glu
1               5                   10                  15

His Lys Asp Asn Ile Arg Arg Tyr Leu Thr Gln Glu Thr Asn Lys
                20                  25                  30

Val Arg Arg Ile Leu Glu Gln Ser Gly Glu Trp Trp Lys
            35                  40                  45
```

<210> SEQ ID NO 45
<211> LENGTH: 45
<212> TYPE: PRT
<213> ORGANISM: Artificial
<220> FEATURE:
<223> OTHER INFORMATION: synthetic peptide

<400> SEQUENCE: 45

```
Lys Leu Val Glu Arg Leu Gly Ala Ala Arg Arg Tyr Leu Thr Gln
1               5                   10                  15

Glu Thr Asn Lys Val Arg Arg Asp Tyr Val Arg Glu His Lys Asp Asn
                20                  25                  30

Ile Arg Arg Ile Leu Glu Gln Ser Gly Glu Trp Trp Lys
            35                  40                  45
```

<210> SEQ ID NO 46
<211> LENGTH: 45
<212> TYPE: PRT
<213> ORGANISM: Artificial
<220> FEATURE:
<223> OTHER INFORMATION: synthetic peptide

<400> SEQUENCE: 46

```
Asp Tyr Val Arg Glu His Lys Asp Asn Ile Arg Arg Lys Leu Val Glu
1               5                   10                  15

Arg Leu Gly Ala Ala Arg Arg Arg Tyr Leu Thr Gln Glu Thr Asn Lys
                20                  25                  30

Val Arg Arg Ile Leu Glu Gln Ser Gly Glu Trp Trp Lys
            35                  40                  45
```

<210> SEQ ID NO 47
<211> LENGTH: 45

```
<212> TYPE: PRT
<213> ORGANISM: Artificial
<220> FEATURE:
<223> OTHER INFORMATION: synthetic peptide

<400> SEQUENCE: 47

Asp Tyr Val Arg Glu His Lys Asp Asn Ile Arg Arg Arg Tyr Leu Thr
 1               5                  10                  15
Gln Glu Thr Asn Lys Val Arg Arg Lys Leu Val Glu Arg Leu Gly Ala
            20                  25                  30
Ala Arg Arg Ile Leu Glu Gln Ser Gly Glu Trp Trp Lys
        35                  40                  45

<210> SEQ ID NO 48
<211> LENGTH: 45
<212> TYPE: PRT
<213> ORGANISM: Artificial
<220> FEATURE:
<223> OTHER INFORMATION: synthetic peptide

<400> SEQUENCE: 48

Arg Tyr Leu Thr Gln Glu Thr Asn Lys Val Arg Arg Lys Leu Val Glu
 1               5                  10                  15
Arg Leu Gly Ala Ala Arg Arg Asp Tyr Val Arg Glu His Lys Asp Asn
            20                  25                  30
Ile Arg Arg Ile Leu Glu Gln Ser Gly Glu Trp Trp Lys
        35                  40                  45

<210> SEQ ID NO 49
<211> LENGTH: 45
<212> TYPE: PRT
<213> ORGANISM: Artificial
<220> FEATURE:
<223> OTHER INFORMATION: synthetic peptide

<400> SEQUENCE: 49

Arg Tyr Leu Thr Gln Glu Thr Asn Lys Val Arg Asp Tyr Val Arg
 1               5                  10                  15
Glu His Lys Asp Asn Ile Arg Arg Lys Leu Val Glu Arg Leu Gly Ala
            20                  25                  30
Ala Arg Arg Ile Leu Glu Gln Ser Gly Glu Trp Trp Lys
        35                  40                  45

<210> SEQ ID NO 50
<211> LENGTH: 45
<212> TYPE: PRT
<213> ORGANISM: Artificial
<220> FEATURE:
<223> OTHER INFORMATION: synthetic peptide

<400> SEQUENCE: 50

Asp Tyr Val Arg Glu His Lys Asp Asn Ile Arg Arg Asn Tyr Ser Val
 1               5                  10                  15
Arg Tyr Arg Pro Gly Leu Arg Arg Leu Gln Glu Trp Cys Ser Val
            20                  25                  30
Ile Arg Arg Ile Leu Glu Gln Ser Gly Glu Trp Trp Lys
        35                  40                  45

<210> SEQ ID NO 51
<211> LENGTH: 45
<212> TYPE: PRT
<213> ORGANISM: Artificial
<220> FEATURE:
```

<223> OTHER INFORMATION: synthetic peptide

<400> SEQUENCE: 51

Asp Tyr Val Arg Glu His Lys Asp Asn Ile Arg Arg Leu Gln Glu
1               5                   10                  15

Trp Cys Ser Val Ile Arg Arg Asn Tyr Ser Val Arg Tyr Arg Pro Gly
                20                  25                  30

Leu Arg Arg Ile Leu Glu Gln Ser Gly Glu Trp Trp Lys
        35                  40                  45

<210> SEQ ID NO 52
<211> LENGTH: 45
<212> TYPE: PRT
<213> ORGANISM: Artificial
<220> FEATURE:
<223> OTHER INFORMATION: synthetic peptide

<400> SEQUENCE: 52

Asn Tyr Ser Val Arg Tyr Arg Pro Gly Leu Arg Arg Asp Tyr Val Arg
1               5                   10                  15

Glu His Lys Asp Asn Ile Arg Arg Leu Gln Glu Trp Cys Ser Val
                20                  25                  30

Ile Arg Arg Ile Leu Glu Gln Ser Gly Glu Trp Trp Lys
        35                  40                  45

<210> SEQ ID NO 53
<211> LENGTH: 45
<212> TYPE: PRT
<213> ORGANISM: Artificial
<220> FEATURE:
<223> OTHER INFORMATION: synthetic peptide

<400> SEQUENCE: 53

Asn Tyr Ser Val Arg Tyr Arg Pro Gly Leu Arg Arg Leu Gln Glu
1               5                   10                  15

Trp Cys Ser Val Ile Arg Arg Asp Tyr Val Arg Glu His Lys Asp Asn
                20                  25                  30

Ile Arg Arg Ile Leu Glu Gln Ser Gly Glu Trp Trp Lys
        35                  40                  45

<210> SEQ ID NO 54
<211> LENGTH: 45
<212> TYPE: PRT
<213> ORGANISM: Artificial
<220> FEATURE:
<223> OTHER INFORMATION: synthetic peptide

<400> SEQUENCE: 54

Arg Leu Gln Glu Trp Cys Ser Val Ile Arg Asn Tyr Ser Val Arg
1               5                   10                  15

Tyr Arg Pro Gly Leu Arg Arg Asp Tyr Val Arg Glu His Lys Asp Asn
                20                  25                  30

Ile Arg Arg Ile Leu Glu Gln Ser Gly Glu Trp Trp Lys
        35                  40                  45

<210> SEQ ID NO 55
<211> LENGTH: 45
<212> TYPE: PRT
<213> ORGANISM: Artificial
<220> FEATURE:
<223> OTHER INFORMATION: synthetic peptide

<400> SEQUENCE: 55

```
Arg Leu Gln Glu Trp Cys Ser Val Ile Arg Arg Asp Tyr Val Arg Glu
1               5                   10                  15

His Lys Asp Asn Ile Arg Arg Asn Tyr Ser Val Arg Tyr Arg Pro Gly
            20                  25                  30

Leu Arg Arg Ile Leu Glu Gln Ser Gly Glu Trp Trp Lys
        35                  40                  45
```

<210> SEQ ID NO 56
<211> LENGTH: 44
<212> TYPE: PRT
<213> ORGANISM: Artificial
<220> FEATURE:
<223> OTHER INFORMATION: synthetic peptide

<400> SEQUENCE: 56

```
Val Tyr Asp Tyr Asn Cys His Val Asp Leu Arg Arg Tyr Leu Thr
1               5                   10                  15

Gln Glu Thr Asn Lys Val Arg Arg Asp Tyr Ser Ala Arg Trp Asn Glu
            20                  25                  30

Ile Arg Arg Gln Ile Arg Pro Ile Phe Ser Asn Arg
        35                  40
```

<210> SEQ ID NO 57
<211> LENGTH: 44
<212> TYPE: PRT
<213> ORGANISM: Artificial
<220> FEATURE:
<223> OTHER INFORMATION: synthetic peptide

<400> SEQUENCE: 57

```
Val Tyr Asp Tyr Asn Cys His Val Asp Leu Arg Arg Asp Tyr Ser Ala
1               5                   10                  15

Arg Trp Asn Glu Ile Arg Arg Arg Tyr Leu Thr Gln Glu Thr Asn Lys
            20                  25                  30

Val Arg Arg Gln Ile Arg Pro Ile Phe Ser Asn Arg
        35                  40
```

<210> SEQ ID NO 58
<211> LENGTH: 43
<212> TYPE: PRT
<213> ORGANISM: Artificial
<220> FEATURE:
<223> OTHER INFORMATION: synthetic peptide

<400> SEQUENCE: 58

```
Lys Leu Val Glu Arg Leu Gly Ala Ala Arg Arg Leu Tyr Ala Trp Glu
1               5                   10                  15

Pro Ser Phe Leu Arg Arg Val Tyr Asp Tyr Asn Cys His Val Asp Leu
            20                  25                  30

Arg Arg Asp Tyr Ser Ala Arg Trp Asn Glu Ile
        35                  40
```

<210> SEQ ID NO 59
<211> LENGTH: 43
<212> TYPE: PRT
<213> ORGANISM: Artificial
<220> FEATURE:
<223> OTHER INFORMATION: synthetic peptide

<400> SEQUENCE: 59

```
Leu Tyr Ala Trp Glu Pro Ser Phe Leu Arg Arg Lys Leu Val Glu Arg
1               5                   10                  15
```

```
Leu Gly Ala Ala Arg Arg Val Tyr Asp Tyr Asn Cys His Val Asp Leu
            20                  25                  30

Arg Arg Asp Tyr Ser Ala Arg Trp Asn Glu Ile
        35                  40
```

<210> SEQ ID NO 60
<211> LENGTH: 46
<212> TYPE: PRT
<213> ORGANISM: Artificial
<220> FEATURE:
<223> OTHER INFORMATION: synthetic peptide

<400> SEQUENCE: 60

```
Arg Arg Arg Leu Tyr Ala Trp Glu Pro Ser Phe Leu Arg Arg Arg Leu
1               5                   10                  15

Gln Glu Trp Cys Ser Val Ile Arg Arg Asp Tyr Leu Arg Ser Val Leu
            20                  25                  30

Glu Asp Phe Arg Arg Ala Ser Leu Asp Ser Asp Pro Trp Val
        35                  40                  45
```

<210> SEQ ID NO 61
<211> LENGTH: 47
<212> TYPE: PRT
<213> ORGANISM: Artificial
<220> FEATURE:
<223> OTHER INFORMATION: synthetic peptide

<400> SEQUENCE: 61

```
Arg Arg Arg Arg Leu Tyr Ala Trp Glu Pro Ser Phe Leu Arg Arg Arg
1               5                   10                  15

Leu Gln Glu Trp Cys Ser Val Ile Arg Arg Asp Tyr Leu Arg Ser Val
            20                  25                  30

Leu Glu Asp Phe Arg Arg Ala Ser Leu Asp Ser Asp Pro Trp Val
        35                  40                  45
```

<210> SEQ ID NO 62
<211> LENGTH: 46
<212> TYPE: PRT
<213> ORGANISM: Artificial
<220> FEATURE:
<223> OTHER INFORMATION: synthetic peptide

<400> SEQUENCE: 62

```
Leu Tyr Ala Trp Glu Pro Ser Phe Leu Arg Arg Arg Leu Gln Glu
1               5                   10                  15

Trp Cys Ser Val Ile Arg Arg Asp Tyr Leu Arg Ser Val Leu Glu
            20                  25                  30

Asp Phe Arg Arg Ala Ser Leu Asp Ser Asp Pro Trp Val
        35                  40                  45
```

<210> SEQ ID NO 63
<211> LENGTH: 46
<212> TYPE: PRT
<213> ORGANISM: Artificial
<220> FEATURE:
<223> OTHER INFORMATION: synthetic peptide

<400> SEQUENCE: 63

```
Arg Arg Arg Asp Tyr Ser Ala Arg Trp Asn Glu Ile Arg Arg Gln Ile
1               5                   10                  15

Arg Pro Ile Phe Ser Asn Arg Arg Arg Val Tyr Asp Tyr Asn Cys His
            20                  25                  30
```

Val Asp Leu Arg Arg Leu Leu Gln Ala Glu Ala Pro Arg Leu
    35                  40                  45

<210> SEQ ID NO 64
<211> LENGTH: 47
<212> TYPE: PRT
<213> ORGANISM: Artificial
<220> FEATURE:
<223> OTHER INFORMATION: synthetic peptide

<400> SEQUENCE: 64

Arg Arg Arg Arg Asp Tyr Ser Ala Arg Trp Asn Glu Ile Arg Arg Gln
1               5                   10                  15

Ile Arg Pro Ile Phe Ser Asn Arg Arg Val Tyr Asp Tyr Asn Cys
            20                  25                  30

His Val Asp Leu Arg Arg Leu Leu Gln Ala Glu Ala Pro Arg Leu
        35                  40                  45

<210> SEQ ID NO 65
<211> LENGTH: 48
<212> TYPE: PRT
<213> ORGANISM: Artificial
<220> FEATURE:
<223> OTHER INFORMATION: synthetic peptide

<400> SEQUENCE: 65

Arg Arg Arg Asp Tyr Val Arg Glu His Lys Asp Asn Ile Arg Arg Arg
1               5                   10                  15

Tyr Leu Thr Gln Glu Thr Asn Lys Val Arg Arg Lys Leu Val Glu Arg
            20                  25                  30

Leu Gly Ala Ala Arg Arg Ile Leu Glu Gln Ser Gly Glu Trp Trp Lys
        35                  40                  45

<210> SEQ ID NO 66
<211> LENGTH: 49
<212> TYPE: PRT
<213> ORGANISM: Artificial
<220> FEATURE:
<223> OTHER INFORMATION: synthetic peptide

<400> SEQUENCE: 66

Arg Arg Arg Arg Asp Tyr Val Arg Glu His Lys Asp Asn Ile Arg Arg
1               5                   10                  15

Arg Tyr Leu Thr Gln Glu Thr Asn Lys Val Arg Arg Lys Leu Val Glu
            20                  25                  30

Arg Leu Gly Ala Ala Arg Arg Ile Leu Glu Gln Ser Gly Glu Trp Trp
        35                  40                  45

Lys